United States Patent
Mier et al.

(10) Patent No.: US 10,363,323 B2
(45) Date of Patent: Jul. 30, 2019

(54) HYDROPHOBIC MODIFIED PEPTIDES FOR LIVER SPECIFIC DIAGNOSIS

(75) Inventors: Walter Mier, Bensheim (DE); Stephan Urban, Neustadt/Weinstrasse (DE); Stefan Mehrle, Limburgerhof (DE); Uwe Haberkorn, Schweitzingen (DE); Thomas Müller, Schriesheim (DE); Vasileios Askoxylakis, Wilhelmsfeld (DE)

(73) Assignee: RUPRECHT-KARLS-UNIVERSITAT HEIDELBERG, Heidelberg (DE)

( * ) Notice: Subject to any disclaimer, the term of this patent is extended or adjusted under 35 U.S.C. 154(b) by 0 days.

(21) Appl. No.: 13/984,715

(22) PCT Filed: Feb. 10, 2012

(86) PCT No.: PCT/EP2012/052343
§ 371 (c)(1),
(2), (4) Date: Aug. 21, 2014

(87) PCT Pub. No.: WO2012/107577
PCT Pub. Date: Aug. 16, 2012

(65) Prior Publication Data
US 2014/0356284 A1    Dec. 4, 2014

Related U.S. Application Data

(60) Provisional application No. 61/441,499, filed on Feb. 10, 2011.

(51) Int. Cl.
| | | |
|---|---|---|
| *A61K 51/08* | (2006.01) | |
| *A61K 38/00* | (2006.01) | |
| *A61K 49/00* | (2006.01) | |
| *A61K 49/08* | (2006.01) | |
| *A61K 49/14* | (2006.01) | |
| *C07K 14/005* | (2006.01) | |
| *C12N 7/00* | (2006.01) | |

(52) U.S. Cl.
CPC ........ *A61K 51/088* (2013.01); *A61K 49/0056* (2013.01); *A61K 49/085* (2013.01); *A61K 49/14* (2013.01); *C07K 14/005* (2013.01); *C12N 7/00* (2013.01); *A61K 38/00* (2013.01); *C07K 2319/50* (2013.01); *C12N 2730/10122* (2013.01); *Y02A 50/409* (2018.01); *Y02A 50/411* (2018.01); *Y02A 50/423* (2018.01); *Y02A 50/463* (2018.01)

(58) Field of Classification Search
None
See application file for complete search history.

(56) References Cited

FOREIGN PATENT DOCUMENTS

| | | |
|---|---|---|
| JP | 2001-523961 | 11/2001 |
| JP | 2007-525997 | 9/2007 |
| JP | 2007-535492 | 12/2007 |
| JP | 2008-516896 | 5/2008 |
| JP | 2010-518115 | 5/2010 |
| JP | 2014-506574 | 3/2014 |
| JP | 2014-510050 | 4/2014 |
| JP | 2017-101031 | 6/2017 |
| WO | 2009/092611 | 7/2009 |
| WO | WO 2009/092396 | 7/2009 |
| WO | WO 2009/092612 | 7/2009 |
| WO | 2009/100934 | 8/2009 |
| WO | 2010/088411 | 8/2010 |

OTHER PUBLICATIONS

De León-Rodríguez et al., "Solid-Phase Synthesis of DOTA-Peptides", Chem. Eur. J., 2004, pp. 1149-1155 (Year: 2004).*
Chinese Office Action, Chinese Patent Application No. 201280008451. 9, dated Apr. 6, 2016, pp. 1-8, Chinese Patent Office, China.
Glebe et al., Mapping of the Hepatitis B Virus Attachment Site by Use of Infection-Inhibiting preS1 Lipopeptides and Tupaia Hepatocytes, American Gastroenterological Association, 2005, pp. 234-245.
Luis M De Leon-Rodriguez and Zoltan Kovacs: "The Synthesis and Chelation Chemistry of DOTA", Bioconjugate Chemistry, ACS, Washington, DC, US, vol. 19, No. 2, Feb. 1, 2008 (Feb. 1, 2008), pp. 391-402, XP008146824, ISSN: 1043-1802, DOI: 10.1021/BC700328S.
Official action from related JP 2014-506574 dated Dec. 8, 2015, 6 pages.
"Development of a novel fluorogenic proteolytic beacon for in vivo detection and imaging of tumour-associated matrix metalloproteinase-7 activity", Biochemical Journal, 2004, vol. 377, pp. 617-628.
"Peptide-Mediated Targeted Drug Delivery", Medicinal Research Reviews, vol. 32, No. 3, pp. 637-658, published online Sep. 2, 2010.

* cited by examiner

*Primary Examiner* — Lianko G Garyu
(74) *Attorney, Agent, or Firm* — Barnes & Thornburg LLP

(57) ABSTRACT

The present invention relates to hydrophobic modified peptides for the specific delivery of labels to the liver, preferably to hepatocytes, in vitro as well as in vivo. The present invention relates to pharmaceutical compositions comprising said hydrophobic modified peptide(s) and the label(s) to be specifically delivered to the liver. The present invention furthermore relates to the diagnostic use of the inventive hydrophobic modified peptides as well as to a method for the diagnosis of liver diseases or disorders.

40 Claims, 9 Drawing Sheets
Specification includes a Sequence Listing.

HYDROPHOBIC MODIFIED PEPTIDES FOR LIVER SPECIFIC DIAGNOSIS

CROSS-REFERENCE TO RELATED APPLICATIONS

This application is a US National Phase filing of PCT/EP2012/052343, filed on Feb. 10, 2012, which claims priority to U.S. 61/441,499, filed on Feb. 10, 2011. The disclosure therein is expressly incorporated entirely by reference.

The present invention relates to hydrophobic modified peptides derived from the preS domain of hepatitis B virus (HBV) which are versatile vehicles for the specific delivery of a labelling compound (diagnostic agents, in the following "label") to the liver, preferably to hepatocytes, in vitro as well as in vivo. Any kind of label can be specifically targeted to the liver and so be enriched in the liver. This liver targeting can further be used for the targeted diagnosis of liver diseases or disorders, such as hepatitis, malaria, hepatocellular carcinoma (HCC), as well as HAV, HBV, HCV and/or HDV infection. The present invention relates to pharmaceutical compositions comprising said hydrophobic modified peptide(s) and the label(s) to be specifically delivered to the liver. The present invention furthermore relates to the use of the inventive hydrophobic modified peptides or pharmaceutical compositions comprising said hydrophobic modified peptide(s) for the diagnosis, and/or monitoring of a treatment of a liver disease or disorder; and the use of the inventive hydrophobic modified peptides for the manufacture of a medicament for the diagnosis, and/or monitoring of a treatment of a liver disease or disorder; and to a method for the diagnosis of liver diseases or disorders or the monitoring of a treatment of a liver disease or disorder.

BACKGROUND OF THE INVENTION

The liver, an organ which is present in vertebrates and other animals, plays a major role in the metabolism and has a number of functions in the body, including glycogen storage, decomposition of red blood cells, synthesis of plasma proteins, and detoxification. The liver also is the largest gland in the human body. It lies below the diaphragm in the thoracic region of the abdomen. It produces bile, an alkaline compound which aids in digestion, via the emulsification of lipids. It also performs and regulates a wide variety of high-volume biochemical reactions requiring specialized tissues.

Hepatocytes make up 70 to 80% of the cytoplasmic mass of the liver. Hepatocytes are involved in protein synthesis, protein storage and transformation of carbohydrates, synthesis of cholesterol, bile salts and phospholipids, and detoxification, modification and excretion of exogenous and endogenous substances. The hepatocyte also initiates the formation and secretion of bile.

There are a wide number of known liver diseases, such as:
Hepatitis: inflammation of the liver, caused mainly by various viruses but also by certain poisons, autoimmunity or hereditary conditions;
Cirrhosis: the formation of fibrous tissue in the liver, replacing dead liver cells. The death of the liver cells can for example be caused by viral hepatitis, alcoholism or contact with other liver-toxic chemicals;
Haemochromatosis: a hereditary disease causing the accumulation of iron in the body, eventually leading to liver damage;
Cancer of the liver: primary hepatocellular carcinoma (HCC) or cholangiocarcinoma and metastatic cancers, usually from other parts of the gastrointestinal tract;
Wilson's disease: a hereditary disease which causes the body to retain copper;
Primary sclerosing cholangitis: an inflammatory disease of the bile duct, autoimmune in nature;
Primary biliary cirrhosis: autoimmune disease of small bile ducts;
Budd-Chiari syndrome: obstruction of the hepatic vein;
Gilbert's syndrome: a genetic disorder of bilirubin metabolism, found in about 5% of the population;
Glycogen storage disease type II: the build-up of glycogen causes progressive muscle weakness (myopathy) throughout the body and affects various body tissues, particularly in the heart, skeletal muscles, liver and nervous system.

There are also many pediatric liver diseases, such as biliary atresia, alpha-1-antitrypsin deficiency, alagille syndrome, and progressive familial intrahepatic cholestasis; as well as metabolic diseases.

Furthermore, several pathogens and parasites, especially of tropical diseases, have a liver stage during their life cycle. For instance malaria, is one of the most common infectious diseases and an enormous public-health problem. Malaria is caused by protozoan parasites of the genus *Plasmodium*. The most serious forms of the disease are caused by *Plasmodium falciparum* and *Plasmodium vivax*, but other related species (*Plasmodium ovale, Plasmodium malariae*, and sometimes *Plasmodium knowlesi*) can also infect humans.

Another example is Hepatitis B virus (HBV), the cause for hepatitis B. HBV is the prototype of a family of small, enveloped DNA viruses of mammals and birds (11). The HBV envelope encloses three proteins termed L-(large), M-(middle) and S-(small) (see FIG. 1). They share the C-terminal S-domain with four transmembrane regions. The M- and L-protein carry additional N-terminal extensions of 55 and, genotype-dependent, 107 or 118 aa (preS2- and preS1). In virions the stoichiometric ratio of L, M and S is about 1:1:4, while the more abundantly secreted non-infectious subviral particles (SVPs) contain almost exclusively S- and only traces of L-protein (2). During synthesis, the preS1-domain of L is myristoylated and at some point of the HBV life cycle translocated through the ER-derived membrane. This modification is essential for infectivity (13, 14). A pronounced feature of HBV is its liver tropism, i.e. the liver is the tissue which specifically supports the growth of HBV.

Chronic HBV and HCV (Hepatitis C Virus) infections are also major causes for neoplastic alterations in the liver. Primary hepatocellular carcinoma (HCC), usually develop in the setting of chronic liver disease, particular of viral hepatitis. HCC diagnosis can be difficult, usually requiring the use of serum markers and imaging modalities as well as histologic confirmation following biopsy.

HCC results into about one million deaths per annum globally, the median survival following diagnosis is approximately 6 to 20 months (11). One reason for this is the absence of pathogenic symptoms and the liver's large functional reserve (12). As a result the majority of patients diagnosed with hepatocellular carcinoma are not eligible for surgical resection but require other treatment modalities such as liver transplantation, radiofrequency ablation, transarterial chemoembolization, cryoablation or radiation therapy. All of these alternative options are of limited efficacy due to the typically large tumour size at the time of diagnosis. (13) As a consequence the FDA (Federal Drug Agency) recommends intense diagnostic imaging in patients with an underlying liver disease (i.e. cirrhosis, viral hepatitis) who develops a rising serum alpha-fetoprotein level. (12) Diagnostic imaging is usually performed by CT scan of the liver and/or magnetic resonance imaging (MRI). However the initial diagnosis even when using high resolution imaging methods is often difficult as such "follow up" imaging is recommended in the majority of all patients. (14) Novel liver specific contrast agents such as the one described in the invention may help elevate this problem.

Another source for neoplastic alterations in the liver is metastatic spread of primary tumours of other organs, most prominently metastatic spread of colorectal carcinoma (CRC). CRCs are the third most common cause of cancer related death worldwide. About 1.25 million patients develop colorectal cancer per annum; more than 600.000 patients die per year. (Source: GLOBOCAN 2008, globocan.iarc.fr). While the pathogenesis of CRCs is mostly cleared up by now and the FDA recommends regular medical examination for all people from the age of 50 the incidence rate decreased only mildly from 1997 to 2008. (15, 16).

Following primary diagnosis about 80% of all patients do present without any detectable metastasis, for those patients surgical resection is the best therapeutic option. Despite resection more than 40% of all patients diagnosed with TMN classification II/III develop metastasis in the liver (17-21). It has been shown that intensive high resolution imaging following primary resection can significantly enhance the survival time of patients classified in TMN II/III. Early diagnosis of small metastasis in the liver can enhance 5 year survival time following partial hepatectomy by 40% when compared to conventional care. However due to the amorphous structure of the liver early stage diagnosis is often not possible (22). Contrast agents such as the one described herein can help to diagnose liver metastasis in an early stage, allowing surgical intervention and by this help to enhance disease free survival.

Ideally, drug targeting should fulfil the following criteria: 1) exclusive transfer of the drug (e.g. a label) to the required site of action; 2) a minimum of effects for the remaining organism; 3) use of a pharmacologically inactive vector.

In order to carry a label to a specific tissue different strategies are pursued. These are for example the use of prodrugs, from which the pharmacologically active part is released in the target tissue by tissue-specific enzymes. A further possibility is to couple effective, non-tissue-specific drugs to tissue-specific, but pharmacologically inert carrier systems like receptor-affine peptides or colloidal particles.

Various drug carriers have been used to enhance liver targeting of drugs. A straightforward approach is based on the active phagocytosis of the reticuloendothelial system in the liver by delivering drugs in particular carriers, such as liposomes and microspheres. For example, it has been shown that following i.v. (intravenous) injection, particulate carriers incorporating a drug are mainly captured by the reticuloendothelial system in the liver, resulting in drug targeting of the liver (5). On the other hand, liver targeting of drugs with positively charged, water-soluble polymers is based on free extravasation of most water-soluble substances from the vascular system of the liver as well as on negative charges on the liver cell surface (6). Thus, polymers have been used as the carrier to allow drugs to target to the liver based on such anatomical and biochemical characteristics of the liver. More specific drug targeting of the liver has been attempted by using asialoglycoprotein receptors of liver cells. The asialoglycoprotein receptor (galactose receptor) is present on hepatocytes with high density. In addition, once a ligand binds to the galactose receptor, the ligand-receptor complex is internalized which allows the cellular uptake of galactosylated ligands (7). Furthermore delivery approaches using nanoparticles have been performed by e.g. amphilic polymers and viral vectors (8). Also delivery of drugs and genetic material has been conducted via the use of bio-nanocapsules (BNCs). BNCs are described as "nano-scaled capsules consisting of proteins produced by biotechnological techniques" and can be used as delivery systems for organ specific drug delivery (9).

U.S. Pat. No. 7,001,760 B2 disclose recombinant vectors derived from hepatitis B virus (HBV), which can be used for gene therapy, such as the delivery of therapeutic genes to liver cells and the expression of heterologous genes in liver cells.

WO2009/092612, whose content is incorporated herewith by reference in its entirety, describes hydrophobic modified preS-derived peptides of HBV and their use as vehicles for the specific delivery of compounds to the liver. In this document, the hydrophobic modified preS-derived peptides of HBV may be coupled with a diagnostic or therapeutic active agent via an optional anchor group (A) which is preferably "C-terminal" of the hydrophobic modified preS-derived peptide.

The present invention provides hydrophobic modified peptides conjugated to one ore more label which label is coupled to the N-terminal amino acid sequence of the peptide represented by X, making it possible to create shorter peptides while still maintaining liver specificity. Surprisingly it has become possible to couple hydrophobic moieties to the peptides without abrogating liver tropism. Furthermore, coupling labels to the N-terminal site allows better delivery of active compounds across the cell membrane and also allows to direct labels, which are active on the cellular membrane, directly to the site of action. In FIG. 3, the molecular mechanism of the binding of a hydrophobic modified peptide to the surface of a hepatocyte is schematically illustrated.

SUMMARY OF THE INVENTION

According to the present invention this object is solved by providing a hydrophobic modified peptide. In FIG. 2, the construction of a hydrophobic modified peptide of the invention is schematically illustrated. Said hydrophobic modified peptide has the general formula: $[X-P-Y-R_o]A_p$ wherein P is a peptide of SEQ ID NO: 1 having the amino acid sequence NPLGFXaaP (single-letter code; wherein Xaa is an arbitrary amino acid, preferably F or L, more preferably F). X is an amino acid sequence having a length of m amino acids, wherein one or more of the amino acids of X carry one or more group for hydrophobic modification selected from acylation, preferably with carboxylic acids, saturated and unsaturated fatty acids, C8 to C22 fatty acids, amino acids with lipophilic side chains, and addition of hydrophobic moieties selected from cholesterol, derivatives of cholesterol, phospholipids, glycolipids, glycerol esters, steroids, ceramids, isoprene derivatives, adamantane, farnesol, aliphatic groups, polyaromatic compounds and m is at least 4 (m is ≥4). In a preferred embodiment the hydrophobic modification is effected by acylation with acyl moieties, preferably selected from myristoyl (C 14), palmitoyl (C 16) or stearoyl (C 18), more preferably by acylation with myristoyl (C 14) or by acylation with stearoyl (C 18). Y is an amino acid sequence having a length of n amino acids, (n is 0 or at least 1). In the above general formula m+n are at least 11, that is, the hydrophobic modified peptide of the invention has a length of at least 18 amino acids (aa) in total. R is a C-terminal modification of said hydrophobic modified peptide, which is preferably a moiety that protects from degradation selected from amide, D-amino acid, modified amino acid, cyclic amino acid, albumin, natural and synthetic polymer, such as PEG, glycane (o is 0 or at least 1). A is an anchor group, preferably selected from ester, ether, disulfide, amide, thiol, thioester, p is 0 or at least 1. In a preferred embodiment m is 4 to 19 and/or n is 0 to 78. One or more label(s) is/are coupled to one or amino acid(s) of X. The label may be composed of one substance or may comprise two or more substances, which are linked together by any kind of chemical or physical bond, like covalent bond, ionic bond etc. or the label is in the form of a complex.

In a preferred embodiment of the invention, the one or more label(s) is/are linked to said peptide via a linker or spacer, wherein the linker or spacer is preferably cleaved off the hydrophobic modified peptide by a liver protein, preferably a hepatocellular proteolytic enzyme which may be selected from cytochromes, such as cytochrome P450, proteases and lyases of the endocytic pathway (e.g. estrases), matrix-metallo-proteases MMP1, MMP2, MMP7, MMP9 and MMP12, preferably MMP7. In this case, the linker or spacer preferably comprises the peptide sequences SEQ ID NO: 19 (GCHAK) or SEQ ID NO: 20 (RPLALWRS).

In a further preferred embodiment, the one or more label is/are coupled to one or amino acid(s) of X having an amino group in a side chain, which is/are preferably selected from lysine, α-amino glycine, α,γ-diaminobutyric acid, ornithine, α,β-diaminopropionic acid, more preferably lysine. The amino acid(s) having an amino group in a side chain is/are preferably located at the N-terminus of X, wherein preferably 1 to 11, more preferably 1 to 3, amino acids having an amino group in a side chain are located at the N-terminus of X.

According to the present invention the object is furthermore solved by providing a pharmaceutical composition comprising at least one hydrophobic modified peptide as defined herein and at least a label to be specifically delivered to the liver, preferably to hepatocytes, as defined herein and optionally a pharmaceutically acceptable carrier and/or excipient. In a preferred embodiment, the hydrophobic modified peptide and/or the pharmaceutical composition are used in the specific delivery of label(s) to the liver, preferably for use in the diagnosis or monitoring the treatment of a liver disease or disorder, more preferably in intraoperative visualization.

According to the present invention the object is furthermore solved by providing a use of the hydrophobic modified peptide or the pharmaceutical composition of the invention and the use of the hydrophobic modified peptide for the manufacture of a medicament for the diagnosis, and/or monitoring of a treatment of a liver disease or disorder.

According to the present invention the object is furthermore solved by providing a method for the diagnosis of a liver disease or disorder or for the monitoring of a treatment of a liver disease or disorder, comprising administering to a subject a diagnostically effective amount of a hydrophobic modified peptide or a pharmaceutical composition of the invention.

Further preferred embodiments of the present invention are defined in the dependent claims.

DESCRIPTION OF THE PREFERRED EMBODIMENTS OF THE INVENTION

Before the present invention is described in more detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art. For the purpose of the present invention, all references cited herein are incorporated by reference in their entireties.

Hydrophobic Modified Peptides

As outlined above, the present invention provides hydrophobic modified peptides which are derived from the preS domain of hepatitis B virus (HBV) (also designated "preS-peptides"). The envelope of HBV encloses three proteins termed L (large), M (middle) and S (small) (see FIG. 1). They share the C-terminal S-domain with four transmembrane regions. The M- and L-protein carry additional N-terminal extensions of 55 and, genotype-dependent, 107 or 118 amino acids (preS2- and preS1).

Thus, the peptide according to the present invention refers to a peptide with an amino acid sequence that corresponds to or is based on the N-terminal extensions of the L-protein of HBV, preS1, preferably of genotypes A to H as well as of woolly monkey (WMHBV), orangutan, chimpanzee and gorilla hepatitis B viruses, but it also refers to variants thereof, preferably C-terminally truncated variants, amino acid substitution variants. As an indispensible sequence, the amino acid residues being important for the liver tropism of the hydrophobic modified preS-derived peptides of HBV, as set out in SEQ ID NO:1 (NPLGFXP) are present in the amino acid sequence of the hydrophobic modified peptide of the invention. In particular, the hydrophobic modified peptides of the invention are based on the following sequences (amino acids in single letter code; essential domain underlined).

```
Essential domain of the hydrophobic modified peptide (SEQ ID NO: 1):
NPLGFXP
(wherein X is an arbitrary amino acid, preferably F or L, more preferably F)

preS HBV-A (ID: M57663; SEQ ID NO: 2):
MGGWSSKPRKGMGTNLSVPNPLGFFPDHQLDPAFGANSNNPDWDFNPIKDHWPQA

NQVGVGAFGPGFTPPHGGVLGWSPQAQGILATVPAMPPPASTNRQSGRQPTPISPPLR

DSHPQA preS HBV-B (ID: D00329, SEQ ID NO: 3)
MGGWSSKPRKGMGTNLSVPNPLGFFPDHQLDPAFKANSENPDWDLNPHKDNWPDA

HKVGVGAFGPGFTPPHGGLLGWSPQAQGILTSVPAAPPPASTNRQSGRQPTPLSPPLR
```

-continued

```
DTHPQA preS HBV-C (ID: AB048704, SEQ ID NO: 4)
MGGWSSKPRKGMGTNLSVPNPLGFFPDHQLDPAFKANSENPDWDLNPHKDNWPDA

HKVGVGAFGPGFTPPHGGLLGWSPQAQGILTSVPAAPPPASTNRQSGRQPTPLSPPLR

DTHPQA preS HBV-Chimpanzee (ID: AB032432, SEQ ID NO: 5)
MGQNLSTSNPLGFFPEHQLDPAFKANTNNPDWDFNPKKDYWPEANKVGAGAFGPGF

TPPHGGLLGWSPQAQGILTTLPANPPPASTNRQSGRQPTPLSPPLRDTHPQA preS HBV-D (ID: AB048702, SEQ ID NO: 6)
MGQNLSTSNPLGFFPDHQLDPAFRANTNNPDWDFNPNKDTWPDANKVGAGAFGLG

FTPPHGGLLGWSPQAQGIMQTLPANPPPASTNRQSGRQPTPLSPPLRTTHPQA preS HBV-E (ID: X65657, SEQ ID NO: 7)
MGLSWTVPLEWGKNISTTNPLGFFPDHQLDPAFRANTRNPDWDHNPNKDHWTEAN

KVGVGAFGPGFTPPHGGLLGWSPQAQGMLKTLPADPPPASTNRQSGRQPTPITPPLRD

THPQA preS HBV-F (ID: X69798@8, SEQ ID NO: 8)
MGAPLSTTRRGMGQNLSVPNPLGFFPDHQLDPLFRANSSSPDWDFNTNKDSWPMAN

KVGVGGYGPGFTPPHGGLLGWSPQAQGVLTTLPADPPPASTNRRSGRKPTPVSPPLR

DTHPQA preS HBV-G (ID: AF160501, SEQ ID NO: 9)
MGLSWTVPLEWGKNLSASNPLGFLPDHQLDPAFRANTNNPDWDFNPKKDPWPEAN

KVGVGAYGPGFTPPHGGLLGWSPQSQGTLTTLPADPPPASTNRQSGRQPTPISPPLRD

SHPQA

HBV Gibbon (ID: AJ131572, SEQ ID NO: 10)
MGQNHSVTNPLGFFPDHQLDPLFRANSNNPDWDFNPNKDTWPEATKVGVGAFGPGF

TPPHGGLLGWSPQAQGILTTLPAAPPPASTNRQSGRKATPISPPLRDTHPQA

HBV-H (ID: Q8JMY6, SEQ ID NO: 11)
MGAPLSTARRGMGQNLSVPNPLGFFPDHQLDPLFRANSSSPDWDFNTNKDNWPMAN

KVGVGGFGPGFTPPHGGLLGWSPQAQGILTTSPPDPPPASTNRRSGRKPTPVSPPLRDT

HPQA

HBV Orangutan (ID: AF193864, SEQ ID NO: 12)
MGQNLSVSNPLGFFPEHQLDPLFRANTNNPDWDFNPNKDTWPEATKVGVGAFGPGF

TPPHGGLLGWSPQAQGVTTILPAVPPPASTNRQSGRQPTPISPPLRDTHPQA

HBV Woolly Monkey (ID: NC_001896, SEQ ID NO: 13)
MGLNQSTFNPLGFFPSHQLDPLFKANAGSADWDKNPNKDPWPQAHDTAVGAFGPGL

VPPHGGLLGWSSQAQGLSVTVPDTPPPPSTNRDKGRKPTPATPPLRDTHPQA
```

"Variants" are preferably N-terminally and/or C-terminally truncated variants, amino acid substitution or deletion variants, or prolonged variants of the sequences of SEQ ID NOs: 2 to 13, carrying a hydrophobic modification and wherein one or more label(s) is/are coupled to one or amino acid(s) N-terminal of the essential domain of the hydrophobic modified peptide. Variants comprise furthermore an amino acid sequence comprising modified amino acid(s), unnatural amino acid(s) or peptidomimetic(s) or further compounds which can mimic a peptide backbone/structure. Preferably, variants are selected from C-terminally truncated variants of SEQ ID NOs: 2 to 13; amino acid substitution or deletion variants; variants comprising modified amino acid(s), unnatural amino acid(s) or peptidomimetic(s) or further compounds which can mimic a peptide backbone/structure.

According to the invention, a variant of a hydrophobic modified peptide comprise at least the amino acids having the sequence of SEQ ID NO: 1 and can consist of 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118 or 119 amino acids of the above SEQ ID NOs: 2 to 13, or variants thereof.

N-terminally and/or C-terminally truncated variants comprise preferably at least 18 consecutive amino acids, more preferably at least 19 consecutive amino acids, even more preferably at least 20 and just even more preferably at least 21 consecutive amino acids of SEQ ID NOs: 2 to 13 or variants thereof.

The N-terminal sequence (X) of the hydrophobic modified peptide having a length of m amino acids comprises at least 4 amino acids (i.e. m=4). Preferably, the -terminal sequence (X) of the hydrophobic modified peptide can consist of 4, 5, 6, 7, 8, 9, 10, 11, 12, 13, 14, 15, 16, 17, 18, or 19 amino acids. That is, m may be 4 to 19.

In a preferred embodiment, one or amino acid(s) of X have an amino group in a side chain, which is/are preferably selected from lysine, α-amino glycine, α,γ-diaminobutyric acid, ornithine, α,β-diaminopropionic acid, more preferably lysine. The amino acid(s) of X having an amino group in a side chain, is/are preferably is/are located at the N-terminus of X, wherein one to eleven (1-11), preferably one to three (1-3), amino acids having an amino group in a side chain are located at the N-terminus of X.

In a preferred embodiment, the N-terminal sequence (X) of the hydrophobic modified peptide preferably comprises the sequence $NX_1SX_2X_3$ (SEQ ID NO: 16), wherein $X_1$, $X_2$ and $X_3$ may be arbitrary amino acids. Preferably, $X_1$ of SEQ ID NO: 16 is L, I or Q, more preferably L. Preferably, $X_2$ of SEQ ID NO: 16 is T, V, A or is not present, preferably T or V, more preferably T. Preferably, $X_3$ of SEQ ID NO: 16 is P, S, T or F, more preferably P or S, even more preferably S. Preferably, the sequence $NX_1SX_2X_3$ (SEQ ID NO: 16) is directly attached to the N-terminus of the peptide P (SEQ. ID NO: 1; NPLGFXaaP), resulting in a peptide comprising the sequence $NX_1SX_2X_3NPLGFXaaP$ (SEQ ID NO: 22), wherein $X_1$, $X_2$, $X_3$ and Xaa are defined as above.

The C-terminal sequence (Y) of the hydrophobic modified peptide having a length of n amino acids comprises 0 or at least 1 amino acids (i.e. n≥0). Preferably, the -terminal sequence (Y) of the hydrophobic modified peptide can consist of 0, 1, 2, 3, 4, 5, 6, 7, 8, 9, 10, 11, 12, 13, 14, 15, 16, 17, 18, 19 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 78, 79, 80, 81, 82, 83, 84, 85, 86, 87, 88, 89, 90, 91, 92 or 93 amino acids. That is, n may be 0 to 93.

In a preferred embodiment, the C-terminal sequence (Y) of the hydrophobic modified peptide consists of at least 4 amino acids (n=4), which preferably has the sequence $X_4HQLDP$ (SEQ ID NO: 17), wherein $X_4$ is an arbitrary amino acid. Preferably, $X_4$ of SEQ ID NO: 17 is D, E or S, more preferably D or E, even more preferably D. Preferably, the sequence $X_4HQLDP$ (SEQ ID NO: 17) is directly attached to the C-terminus of the peptide P (SEQ. ID NO: 1; NPLGFXaaP), resulting in a peptide comprising the sequence $NPLGFXaaPX_4HQLDP$ (SEQ ID NO: 23), wherein $X_4$ and Xaa are defined as above.

In a preferred embodiment, the hydrophobic modified peptide of the present invention comprises a peptide encoded by the amino acid sequence $NX_1SX_2X_3NPLGFXaaPX_4HQLDP$ (SEQ ID NO: 18), wherein $X_1$, $X_2$, $X_3$, $X_4$ and Xaa are defined as above.

The term "variant" also refers to the homologous sequences found in the different viral species, strains or subtypes of the hepadnavirus genus, such as HBV strain alpha, HBV strain LSH (chimpanzee isolate), woolly monkey HBV (WMHBV), or strains selected from the group consisting of the HBV genotypes A to H (see SEQ ID NOs: 2 to 13).

The term "variant" also refers to homologous sequences which show at least 50% sequence identity to an amino acid sequence comprising the invariant NPLGFXaaP-domain and the adjacent sequences of SEQ ID NOs: 2-13 or any other amino acid sequence disclosed herein, preferably 70%, more preferably 80%, even more preferably 90% or 95%.

Thus, a preferred hydrophobic modified peptide according to the invention comprises a variant of SEQ ID NOs: 2 to 13 with an amino acid sequence of the different viral species, strains or subtypes, preferably of the genotypes of HBV or woolly monkey HBV (WMHBV) or variants thereof.

"Variants" of SEQ ID NOs: 2 to 13 also comprise variants or "analogues" comprising amino acid deletions, amino acid substitutions, such as conservative or non conservative replacement by other amino acids or by isosteres (modified amino acids that bear close structural and spatial similarity to protein amino acids), amino acid additions or isostere additions, as long as the sequence still shows liver tropism, preferably more than 10% of the injected dose accumulates in liver tissue after 1 h following intravenous injection. The liver tropism of the hydrophobic modified peptide or a "variant" thereof is preferably 80% or more of the injected dose/g liver tissue after 1 h, more preferred 90% or more of the injected dose/g liver tissue after 1 h, even more preferred 95% or more of the injected dose/g liver tissue after 1 h.

Conservative amino acid substitutions typically relate to substitutions among amino acids of the same class. These classes include, for example,
  amino acids having uncharged polar side chains, such as asparagine, glutamine, serine, threonine and tyrosine;
  amino acids having basic side chains, such as lysine, arginine, and histidine;
  amino acids having acidic side chains, such as aspartic acid and glutamic acid; and
  amino acids having nonpolar side chains, such as glycine, alanine, valine, leucine, isoleucine, proline, phenylalanine, methionine, tryptophan, and cysteine.

"N-terminal" refers to the N-terminus of X, i.e. the respective first amino acid residue, but comprises also the hydrophobic modification in close proximity to the N-terminus, such as respective amino acid residues (−4), (−3), (−2), (−1), 1, 2 or 3 or 4. Thus, the coupling of the label and the hydrophobic modification can furthermore be obtained by an attachment of a label and a hydrophobic moiety at a site close to the N-terminus of X.

The hydrophobic modification of said hydrophobic modified peptide according to the present invention adds a hydrophobic moiety to the peptide.

X is modified with at least one hydrophobic moiety or group. In preferred embodiments of this invention, X is modified with 1, 2, 3, 4 or more hydrophobic moiety/ies or group(s). That is, X can be modified with more than one hydrophobic moiety or group, such as 2. The hydrophobic moieties or groups can be the same or different to each other. The hydrophobic modification of said peptide according to the present invention is selected from:
  acylation;
  addition of hydrophobic moieties.

Acylation is preferably selected from acylation with carboxylic acids, fatty acids, amino acids with lipophilic side chains. Preferred fatty acids are saturated or unsaturated fatty acids, branched or unbranched fatty acids, preferably with 8 to 22 carbon atoms (C 8 to C 22). More preferably, the hydrophobic modification by acylation is selected from acylation with myristoyl (C 14), palmitoyl (C 16) or stearoyl (C 18). Modification by myristoylation is preferred in in vivo and medicinal applications due to its higher safety, e.g. not showing the adverse effects of the stearoyl group (innate immune response etc). The addition of hydrophobic moieties is preferably selected from addition of cholesterol, derivatives of cholesterol, phospholipids, glycolipids, glycerol esters, steroids, ceramides, isoprene derivatives, adamantane, farnesol, aliphatic groups, polyaromatic compounds. The attachment of the hydrophobic moieties is prefereably by covalent binding, which can be achieved via carbamate, amide, ether, disulfide or any other linkage that is within the skill of the person skilled in the art. Thus, the hydrophobic modified, preferably acylated peptides of this invention are preferably lipopeptides due to their N-terminal lipophilic or hydrophobic group/moiety.

The C-terminal modification (R) of Y is preferably a modification with a moiety that protects from degradation, such as in vivo degradation.

"C-terminal" refers to the modification at the C-terminus, i.e. the respective last amino acid residue, but comprises also the modification in close proximity to the C-terminus, such as the last but one amino acid residue, the last but two amino acid residue or more amino acid residues (e.g. introduction of one D-amino acid that protects the carrier from enzymatic degradation e.g. by the action of carboxypeptidases). The skilled artisan will be able to select the respective suitable moiety(s) depending on the respective application. Preferred moieties that protect from degradation are selected from amides, D-amino acids, modified amino acids, cyclic amino acids, albumin, natural and synthetic polymers, such as PEG, glycane. Furthermore, o is 0 or at least 1, i.e. the C-terminal modification (R) is optional. Preferably, o is 1. In further embodiments of this invention o is 1, 2, 3, 4 or more. That is, the C-terminus of hydrophobic modified peptide or its proximity can be modified with more than one moiety or group, such as 2. The moieties or groups can be the same or different to each other.

In an embodiment of this invention the hydrophobic modification and/or R are linked to the peptide via a linker or spacer. Linker or spacer are known to the skilled artisan, such as polyalanine, polyglycin, carbohydrates, (CHa)n groups. The skilled artisan will, thus, be able to select the respective suitable linker(s) or spacer(s) depending on the respective application.

The optional anchor group (A) serves as an additional point of attachment for a compound, a tag, a label and is located at an amino acid of Y. That is, in case that at least one anchor group (A) is present (i.e. p≥1) Y comprises at least one amino acid, too (i.e. n≥1). In a preferred embodiment, the anchor group is "C-terminal" of Y, wherein "C-terminal" refers to the modification at the C-terminus, i.e. the respective last amino acid residue, but comprises also the close proximity of the C-terminus, such as the last but one amino acid residue, the last but two amino acid residue or more amino acid residues. In this case o can be 0, thus there is no other C-terminal modification R. The anchor group A can be at an amino acid side chain of Y or can be the amino acid side chain of Y itself, i.e. A can be a side chain itself or a modified side chain. The anchor group can also be a modified amino acid residue which was introduced into the amino acid sequence of Y to serve as an anchor group. In other embodiments of the invention the anchor group A is attached to the hydrophobic modification of X and/or the C-terminal modification R. Preferred anchor groups are selected from ester, ether, disulfide, amide, thiol, thioester. The skilled artisan will be able to select the respective suitable anchor group(s) depending on the respective compound, tag, label etc. to be attached. The anchor group can furthermore be suitable for attaching a complex-forming component, such as of the biotin/avidin, polyarginine/oligonucleotide (e.g. siRNA) complex. Furthermore, o is 0 or at least 1, i.e. the anchor group (A) is optional. Preferably, o is 1. In further embodiments of this invention o is 1, 2, 3, 4 or more. That is, there are more than one anchor group, such as 2. The anchor groups can be the same or different to each other, allowing the attachment of several compounds, such as a label or different labels.

Synthesis of the Hydrophobic Modified Peptides

The peptides of the invention can be prepared by a variety of procedures readily known to those skilled in the art, in general by synthetic chemical procedures and/or genetic engineering procedures. Synthetic chemical procedures include more particularly the solid phase sequential and block synthesis (Erickson and Merrifield, 1976). More details can be taken from WO2009/092612.

The solid phase sequential procedure can be performed using established automated methods such as by use of an automated peptide synthesizer. In this procedure an [alpha]-amino protected amino acid is bound to a resin support. The resin support employed can be any suitable resin conventionally employed in the art for the solid phase preparation of (poly)peptides, preferably polystyrene which has been copolymerized with polyoxyethylen to provide sites for ester formation with the initially introduced o-amino protected amino acid. This optimized method, applied by the inventors, has been explicitly described (see e.g. 12). The amino acids are introduced one by one (stepwise). Each synthesis cycle corresponding to the introduction of one amino acid includes a deprotection step, successive washing steps, a coupling step with activation of the amino acid, and subsequent washing steps. Each of these steps is followed by a filtration. The reactive agents for coupling are the classical reactive agents for (poly)peptide synthesis such as dicyclohexylcarbodiimide, hydroxybenzotriazole, benzotriazil-1-yl-oxytris (dimethylamino) phosphonium hexafluorophosphate, and diphenylphosphorylazide. After synthesis of the polypeptide on the resin, the polypeptide is separated from the resin by a treatment with a strong acid such as trifluoroacetic acid in the presence of anisol, ethanedithiol or 2-methylindole. The compound is then purified by the classical techniques of purification, in particular by means of HPLC.

The peptides of the present invention may also be obtained by coupling (poly)peptide fragments that are selectively protected, this coupling being effected e.g. in a solution. The peptides can further be produced by genetic engineering techniques as known to the skilled artisan. A eukaryotic expression system, such as the baculovirus system, is particularly suitable. According to this procedure proteins are expressed in insect cells infected with a recombinant baculovirus containing a nucleic acid sequence encoding a heterologous protein and regulating nucleic acid sequences, such as a promoter. Several cell-lines are available for infection with recombinant baculovirus, such as cell line Sf-9, available from the American Type Culture Collection (CRL 1711). Expression in prokaryotic expression system, such as *E. coli*, is also particularly suitable.

The introduction of the hydrophobic moiety to the peptide can be accomplished by a variety of procedures readily known to those skilled in the art, including synthetic and genetic engineering approaches.

Alternatively, the peptides and/or fusion peptides (i.e. hydrophobic modified peptides) can be produced by stably transfected eukaryotic cell lines, like CHO and other cell lines which are known in the art and usually used for generating vaccines and the like. Due to the intrinsic property that the N-terminal 47-preS1 amino acids promote secretion of a myristoylated protein/peptide, the biologically active hydrophobic modified peptide can be extracted from cell culture supernatants.

Vectors and Shuttles for Liver Targeting

As outlined above, the present invention provides the use of the hydrophobic modified peptides as vehicle or shuttle for the specific delivery of a compound (label) to the liver wherein the label is coupled to the hydrophobic modified peptides as described herein.

"Vehicle" or "shuttle" for the specific delivery of a compound to the liver according to the present invention refers to the liver tropism or hepatotropism of the hydrophobic modified peptides as found by the inventors and described herein, i.e. to their capacity to selectively accumulate in the liver, preferably to selectively accumulate at the plasma membrane of hepatocytes as well as to selectively enter into hepatocytes. The invention is based on the finding of a highly specific liver accumulation and on the identification of the determinants of the liver tropism of HBV in the preS1 sequence of HBV by the inventors. Thus, the invention uses the knowledge about the determinants of the liver tropism for the design of universal vehicles or shuttles for specific liver targeting or delivery, respectively. The hydrophobic modified peptides of the present invention are versatile vehicles or shuttles for specifically delivering compound(s) to the liver.

Preferably, the specific delivery of a compound to the liver is the specific delivery of the compound to hepatocytes. Furthermore, the compound can specifically be delivered to hepatocytes in vitro as well as in vivo. The compound is preferably specifically delivered to the liver of an animal, preferably mammal or human, or a bird.

Labels to be Delivered

The labels to be specifically delivered to the liver according to this invention can be any kind of compound being suitable for diagnostic purposes. Preferably, the label comprises a chelating agent which forms a complex with divalent or trivalent metal cations.

In a preferred embodiment of the invention, the label is selected from a fluorescent dye, a radioisotope and a contrast agent. According to the present invention, a contrast agent is a dye or other substance that helps show abnormal areas inside the body.

Preferred radioisotopes/fluorescence emitting isotopes are selected from the group consisting of alpha radiation emitting isotopes, gamma radiation emitting isotopes, Auger electron emitting isotopes, X-ray emitting isotopes, fluorescence emitting isotopes, such as $^{18}$F, $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{88}$Y, $^{90}$Y, $^{149}$Pm, $^{177}$Lu, $^{47}$Sc, $^{142}$Pr, $^{159}$Gd, $^{212}$Bi, $^{72}$As, $^{72}$Se, $^{97}$Ru, $^{109}$Pd, $^{105}$Rh, $^{101m15}$Rh, $^{119}$Sb, $^{128}$Ba, $^{123}$I, $^{124}$I, $^{131}$I, $^{197}$Hg, $^{211}$At, $^{169}$Eu, $^{203}$Pb, $^{212}$Pb, $^{64}$Cu, $^{67}$Cu, $^{188}$Re, $^{186}$Re, $^{198}$Au and $^{199}$Ag.

Preferred fluorescent dyes are selected from the following classes of dyes: Xanthens (e.g. Fluorescein), Acridines (e.g. Acridine Yellow), Oxazines (e.g. Oxazine 1), Cynines (e.g. Cy7/Cy 3), Styryl dyes (e.g. Dye-28), Coumarines (e.g. Alexa Fluor 350), Porphines (e.g. Chlorophyll B), Metal-Ligand-Complexes (e.g. PtOEPK), Fluorescent proteins (e.g APC, R-Phycoerythrin), Nanocrystals (e.g QuantumDot 705), Perylenes (e.g. Lumogen Red F300) and Phtalocyanines (e.g. IRDYE™700DX) as well as conjugates and combinations of these classes of dyes. Preferred contrast agents are selected from paramagnetic agents, e.g. Gd, Eu, W and Mn, preferably complexed with a chelating agent. Further options are supramagnetic iron (Fe) complexes and particles, compounds containing atoms of high atomic number, i.e. iodine for computer tomography (CT), microbubbles and carriers such as liposomes that contain these contrast agents.

Chelating Agent

The label to be specifically delivered to hepatocytes may be bound to the hydrophobic modified peptide in the form of a complex with a chelating agent being able to form complexes with the respective label. In a preferred embodiment of the invention, the chelating agent is selected from the group consisting of 1,4,7,10-tetraazacyclododecane-N,N',N,N'-tetraacetic acid (DOTA), ethylenediaminetetraacetic acid (EDTA), 1,4,7-triazacyclononane-1,4,7-triacetic acid (NOTA), triethylenetetramine (TETA), iminodiacetic acid, Diethylenetriamine-N,N,N',N',N''-pentaacetic acid (DTPA) and 6-Hydrazinopyridine-3-carboxylic acid (HYNIC), while 1,4,7,10-tetraazacyclododecane-N,N',N,N'-tetraacetic acid (DOTA) is particularly preferred.

Coupling of a Label to the Hydrophobic Modified Peptide

The coupling of the label(s) to the respective amino acids of X may be conducted by any suitable method known to the person skilled in the art.

In a preferred embodiment of the present invention, the label(s) is/are coupled to the respective amino acid of X by using an activated ester. In particular, in case of coupling label(s) to the amino acids of X having an amino group in a side chain this method can be used. Alternatively, the following coupling methods can be used in order to couple one or more label(s) to the respective amino acids of X, which are shortly summarized. The specific reaction conditions for achieving a coupling of a label to an amino acid with or without a linker can be easily determined by a chemist:

- Formation of amides by the reaction of an amine and activated carboxylic acids, preferably NHS-esters or carbodiimides; a carbodiimide is a complete cross-linker that facilitates the direct conjugation of carboxyls to primary amine NHS esters are reactive groups formed by carbodiimide-activation of molecules containing carboxylate groups
- Disulfide linkage using two thiols or one thiol that specifically reacts with pyridyl disulfides; Pyridyl disulfides react with sulfhydryl groups over a broad pH range (the optimum is pH 4-5) to form disulfide bonds. During the reaction, a disulfide exchange occurs between the molecule's SH-group and the 2-pyridyl-dithiol group. As a result, pyridine-2-thione is released.
- Thioether formation using maleimides or haloacetyls and a thiol component; Haloacetyls react with sulfhydryl groups at physiologic pH. The reaction of the iodoacetyl group proceeds by nucleophilic substitution of iodine with a sulfur atom from a sulfhydryl group to result a stable thioether linkage. The maleimide group reacts specifically with sulfhydryl groups when the pH of the reaction mixture is between pH 6.5 and 7.5 and forms a stable thioether linkage that is not reversible.
- Amidine formation using an imidoester and an amine; Imidoester crosslinkers react rapidly with amines at alkaline pH but have short half-lives. As the pH becomes more alkaline, the half life and reactivity with amines increases; therefore, crosslinking is more efficient when performed at pH 10 than at pH 8. Reaction conditions below pH 10 may result in side reactions, although amidine formation is favoured between pH 8-10
- Hydrazide linkage using carbonyls (e.g. aldehydes) and hydrazides; Carbonyls (aldehydes and ketones) react with hydrazides and amines at pH 5-7. Carbonyls do not readily exist in proteins; however, mild oxidation of sugar glycols using sodium meta-periodate converts vicinal hydroxyls to aldehydes or ketones. Subsequent reaction with hydrazides results in the formation of a hydrazone bond.

Amine linkage using carbonyls and amines under reductive conditions; Reductive amination (also known as reductive alkylation) is a form of amination that involves the conversion of a carbonyl group to an amine via an intermediate imine. The carbonyl group is most commonly a ketone or an aldehyde.

Copper-catalyzed triazole formation using nitriles and azides. The Huisgen-type 1,3-dipolar cycloaddition between an azide and a terminal or internal alkyne is used to give stable 1,2,3-triazoles.

Isothiourea formation using isothiocyanates and amines; the reaction between isothiocyanates and amines, i.e. the ε-amino groups of lysine leads to a stable isothiourea bond.

Formation of esters by the reaction of an alcohol and activated carboxylic acids, preferably acid chlorides or carbodiimides; High temperature reaction allows direct reaction between alcohols and carboxylic acids to form stable esters, alternatively the carboxylic acids and be activated under acidic or base catalytic conditions.

Formation of ethers by the reaction of an alcohol and alkyl halides. Haloalkanes are reactive towards nucleophiles. They are polar molecules: the carbon to which the halogen is attached is slightly electropositive where the halogen is slightly electronegative. This results in an electron deficient (electrophilic) carbon which, inevitably, attracts nucleophiles.

Linker/Spacer for the Label

The hydrophobic modified peptide, in particular the conjugates of the present invention, are preferably used to enrich a label that is shuttled to the liver, in the liver. Preferably, the label is cleaved off the hydrophobic modified peptide by a liver protein, preferably a hepatocellular proteolytic enzyme, in particular in vivo in the liver. The label and the hydrophobic modified peptide form a conjugate. Preferably, the conjugate of label and hydrophobic modified peptide is formed by covalent attachment or by complex formation. The form of attachment depends on the type of label.

The coupling of the label(s) to the respective amino acids of X may be conducted by using a spacer or linker. Linker or spacer are known to the skilled artisan, such as polyalanine, polyglycin, carbohydrates, $(CH_2)n$ groups or amino acid sequences. The skilled artisan will, thus, be able to select the respective suitable linker(s) or spacer(s) depending on the respective application. The spacer or linker preferably comprises a recognition site for hepatocyte specific activation, which is preferably recognized by a liver or tumor specific protein. The recognition site is preferably a proteolytic cleavage site. The liver protein is, thus, preferably a hepatocellular protein, more preferably a hepatocellular proteolytic enzyme or a proteolytic enzyme which is overexpressed in a tumor, e.g. MMP7. Thus, the conjugate can be administered to a subject and will be transported through the body, such as in the body fluids, without being cleaved. However, as soon as the conjugate reaches its target, the liver or the hepatocytes, respectively, the liver protein, such as a hepatocellular proteolytic enzyme will cleave the proteolytic cleavage site and release the label from its shuttle, i.e. the hydrophobic modified peptide.

Further preferred liver proteins are cytochromes, such as cytochrome P450 or lyases of the endocytic pathway. The HepDirect® technology (of Metabasis Technologies, Inc.) as used in Adefovir or Pradevofir, is also suitable for the present invention.

Of particular importance for the diagnosis and prognosis of tumor diseases like neoplastic alterations by metastases of carcinomas, e.g. colon carcinomas, is the interchange between malignant tissue and the surrounding tissue. There is a need for the activation of healthy epithelia cells and or the recruitment of immune cells which is a prerequisite for the formation of a distant metastasis of a primary tumor. Tissue analysis have shown that tumor specific mRNA expression levels of matrix-metallo-proteases (MMP1, MMP2, MMP7, MMP9 and MMP12) are associated with a bad prognosis of tumor patients (Gentner B. et al., Anticancer Res. 2009 January; 29(1):67-74). From theses protease especially MMP7 is of high interest since it is primarily expressed by tumor cells. Coupling a label to the described peptide sequence via a linker sequence containing a specific proteolytic binding site for MMP7 (e.g a short Peptide Sequence SEQ ID NO: 19 (GCHAK) or SEQ ID NO: 20 (RPLALWRS) but also all other MMP 7 substrates (e.g Fibronectin, Elastin, Casein or others) would allow to deliver an inactive label to the liver via the modification of the original peptide by means described above. In the liver the modified peptides would then be preferentially cleaved in the direct surrounding of the tumor tissue and the inactive label would be activated. This method of label delivery to the liver targeting primary hepatocellular carcinomas or metastasis in the liver overexpressing one of the above listed MMPs (e.g. Colon Carcinoma Metastasis) presents a novel way of targeting labels to tumor tissues.

In one embodiment, the conjugate of label and hydrophobic modified derived peptide is formed by complex formation. Preferred complexes useful in the invention are biotin/avidin, polyarginine/oligonucleotide (e.g. siRNA). The skilled artisan will be able to determine suitable complex components and to design the compound and hydrophobic modified peptide accordingly.

Diagnosis of Liver Diseases

In a preferred embodiment of the invention the above hydrophobic modified peptides, in particular their conjugates with labels, are provided for the diagnosis of a liver disease or disorder.

Depending on the liver disease or disorder which shall be diagnosed the respective label is selected and selectively, specifically delivered to the liver. A "liver disease" or a "liver disorder" according to the present invention refers to any disease or disorder that has an effect on or involves the organ liver, liver tissue or hepatocytes.

Examples of liver diseases are:

Cancer of the liver: primary hepatocellular carcinoma (HCC) or cholangiocarcinoma and metastatic cancers, usually from other parts of the gastrointestinal tract; preferentially colorectal carcinoma Hepatitis: inflammation of the liver, caused mainly by various viruses but also by certain poisons, autoimmunity or hereditary conditions;

Cirrhosis: the formation of fibrous tissue in the liver, replacing dead liver cells. The death of the liver cells can for example be caused by viral hepatitis, alcoholism or contact with other liver-toxic chemicals;

Haemochromatosis: a hereditary disease causing the accumulation of iron in the body, eventually leading to liver damage;

Wilson's disease: a hereditary disease which causes the body to retain copper;

Primary sclerosing cholangitis: an inflammatory disease of the bile duct, autoimmune in nature;

Primary biliary cirrhosis: autoimmune disease of small bile ducts;

Budd-Chiari syndrome: obstruction of the hepatic vein;

Gilbert's syndrome: a genetic disorder of bilirubin metabolism, found in about 5% of the population;

Glycogen storage disease type II: the build-up of glycogen causes progressive muscle weakness (myopathy) throughout the body and affects various body tissues, particularly in the heart, skeletal muscles, liver and nervous system;

pediatric liver disease, such as biliary atresia, alpha-1-antitrypsin deficiency, alagille syndrome, and progressive familial intrahepatic cholestasis;

metabolic diseases.

Furthermore, also liver diseases of animals, such as pets or livestock, are included, in particular diseases that can be transmitted to humans, such as toxoplasmosis.

The liver disease or disorder to be diagnosed is preferably selected from Primary Hepatocellular Carcinoma, metastases of other tumours, hepatitis, cirrhosis, haemochromatosis, preferably hepatitis caused by hepatitis A, B, C, D, E, F, G and H virus. The liver disease or disorder to be diagnosed can also be concomitant hepatitis caused by viruses, such as viruses of the family Herpesviridae, e.g. herpes virus, cytomegalic virus (CMV) but also varicella zoster virus (VZV), Epstein Barr virus (EBV), coxsackie viruses, yellow fever virus, Dengue virus.

The liver disease or disorder to be diagnosed can also be a disease which involves a liver stadium of a virus or a non-viral pathogen, such as in many tropical diseases. Since the liver stadium of some pathogens is an early stadium, the respective infection can be selectively, specifically treated in such an early stadium. Such viruses are hepatitis A, B, C, D, E, F, G and H virus, herpes viruses.

Such non-viral pathogens are bacteria, parasites and/or worms. Parasites are for example protozoan parasites of the genus *Plasmodium* that cause malaria, such as *Plasmodium falciparum, Plasmodium vivax*, and related species (e.g. *Plasmodium ovale, Plasmodium malariae, Plasmodium* knowles[iota]). Such worms are for example flatworms of the genus *Schistosoma* that cause schistosomiasis or bilharziosis, such as *Schistosoma mansoni, Schistosoma intercalatum, Schistosoma haematobium, Schistosoma japonicum* and *Schistosoma mekongi*. Such parasites are also for example *Leishmania* trypanosome protozoa of the genus *Phlebotomus* and Lutzomyia which are responsible for the disease leishmaniasis. Therefore, malaria, schistosomiasis (bilharziosis), and/or leishmaniasis can be diagnosed by the means of this invention. Therefore, certain tropical diseases can be diagnosed by the means of this invention.

The liver diseases or disorders to be diagnosed are preferably liver tumors, preferably hepatocellular carcinoma (HCC) or neoplastic alterations by metastases of solid tumors, e.g. colorectal carcinoma.

In a preferred embodiment of the invention the above described hydrophobic modified peptides are used for the early diagnosis and classification of primary neoplastic lesions of the liver, such as early stage hepatocellular carcinoma.

Another preferred embodiment of the invention is the use of the above described hydrophobic modified peptides for the diagnosis of early metastatic lesions in the liver such as metastases of colorectal carcinoma (CRC).

The liver disease or disorder to be diagnosed can also be a metabolic disease, such as diabetes, hyperlipidemia, metabolic syndrome and obesity, chronic hyperglycemia, metabolic syndrome, non-alcoholic steatohepatitis (NASH) (see also (9)).

In a preferred embodiment of the invention the above described hydrophobic modified, preferably acylated derived peptides, in particular their conjugates with labels, can be used for the manufacture of a medicament for the diagnosis of a liver disease or disorder.

Medical Imaging

The hydrophobic modified peptides of the present invention can be used in medical imaging known to those skilled in the art. Suitable methods are X-ray imaging, magnetic resonance imaging (MRI), positron emission tomography (PET), single-photon-emission-computed tomography (SPECT) X-ray computed tomography (CT) and combinations of these methods (e.g. PET-CT, CT-MRI). Specific conditions for conducting these medical imaging methods are known to those skilled in the art.

Pharmaceutical Compositions

As outlined above, the present invention provides a pharmaceutical composition comprising at least one hydrophobic modified peptide as defined herein and at least a compound to be specifically delivered to the liver as defined herein and optionally a pharmaceutically acceptable carrier and/or excipient.

The pharmaceutical composition according to the present invention comprises:

at least one hydrophobic modified peptide as defined herein above; and optionally a pharmaceutically acceptable carrier and/or excipient.

The pharmaceutical compositions according to the present invention are very well suited for all the uses and methods described herein.

A "pharmaceutically acceptable carrier or excipient" refers to any vehicle wherein or with which the pharmaceutical or vaccine compositions according to the invention may be formulated. It includes a saline solution, such as phosphate buffer saline, a citrate buffer, NaCl, ocytl glucoside and/or a poloxamere. In general, a diluent or carrier is selected on the basis of the mode and route of administration, and standard pharmaceutical practice.

Diagnostic Method

Furthermore, and as outlined above, the present invention provides methods for the diagnosis of a liver disease or disorder by utilizing the above described hydrophobic modified peptide(s) or the pharmaceutical composition(s) of the invention.

The present invention also provides a method for the diagnosis of a liver disease or disorder by administering to a subject a hydrophobic modified derived peptide and a label, or a pharmaceutical composition as defined herein. The method for the diagnosis of a liver disease or disorder according to the present invention comprises administering to a subject in a diagnostically effective amount (a) a hydrophobic modified peptide as defined herein above and comprising at least a label as defined herein above, or (b) a pharmaceutical composition as defined herein above.

Route of Administration

Preferably, the route of administration of the hydrophobic modified peptides or pharmaceutical compositions of the present invention, in particular in the method of treatment, is selected from subcutaneous, intravenous, oral, nasal, intramuscular, transdermal, inhalative, by suppository. A preferred embodiment for nasal administration or application is a nasal spray.

In a further preferred embodiment, the hydrophobic modified peptide of the invention comprising a label is dissolved in serum from the patient and is applied via injection.

Diagnostically Effective Amount

A "diagnostically effective amount" of a hydrophobic modified peptide or a pharmaceutical composition of this invention refers to the amount that is sufficient to diagnose the respective liver disease or disorder. The preferred diagnostically effective amount depends on the respective compound that is to be delivered and its respective diagnostic potential. The skilled artisan will be able to determine suitable diagnostically effective amounts. In a preferred embodiment, the diagnostically effective amount is in the range of 10 pmol per kg to 20 μmol per kg body weight. For use as a diagnostic agent (i.e. a label is coupled to the hydrophobic modified peptide) the amount to be applied to a patient is preferably in the range of 100 nmol to 2 μmol more preferably about 500 nmol per kg body weight. When using MRI as the medical imaging method, the respective hydrophobic modified peptide is preferably applied to a patient in an amount ranging from 300 nmol to 800 nmol per kg body weight, more preferably from 400 to 600 nmol per kg body weight.

Preferred Hydrophobic Modified Peptides of the Invention

In the following, preferred hydrophobic modified peptides of the invention are given. These hydrophobic modified peptides are based on the amino acid sequence KKKNLSTSNPLGFFPDHQLPD (SEQ ID NO: 14) or KKKNLSTSNPLGFFPDHQLDP (SEQ ID NO: 15), wherein one or two of the N-terminal lysines (K) may be deleted or substituted by another amino acid. An exemplary preferred hydrophobic modified peptide has the following chemical structure:

The amino acid sequence of the compound having the above exemplified chemical structure is: Stearoyl-K(DOTA[Gd])K(DOTA[Gd])K(DOTA[Gd])NLSTSNPGLGFFPD-HQLDP-amide of SEQ ID NO: 15, wherein each of the three chelating agents 1,4,7,10-tetraazacyclododecane-N,N',N,N'-tetraacetic acid (DOTA) complexes a Gd cation and is bound to one of the three N-terminal lysines (KKK), while the first N-terminal lysine is further modified with a hydrophobic stearoyl group. In this connection it should be noted that the formulas of the hydrophobic modified peptides of the invention are simplified in the text so that the above exemplified hydrophobic modified peptide can be also designated "stearoyl-[K(DOTA [Gd])]$_3$-NLSTSNPLGFFPDHQLDP-amide"

In the following preferred hydrophobic modified peptides of SEQ ID NO: 15 of the invention as well as their specific use in diagnosis of diseases or disorders of the liver are given:

Stearoyl-[K(DOTA[Gd])]$_3$-NLSTSNPLGFFPDHQLDP

Stearoyl-[K(DOTA[$^{68}$Ga])]$_3$-NLSTSNPLGFFPDHQLDP

Stearoyl-[K(DOTA[$^{111}$In])]$_3$-NLSTSNPLGFFPDHQLDP

Stearoyl-[K(DOTA[Gd])]$_3$-NLSTSNPLGFFPDHQLPD

Stearoyl-[K(DOTA[$^{68}$Ga])]$_3$-NLSTSNPLGFFPDHQLPD

Stearoyl-[K(DOTA[$^{111}$In])]$_3$-NLSTSNPLGFFPDHQLPD

Stearoyl-[K(DOTA[Gd])]$_3$-NLSTSNPLGFFPDHQLDP-amide

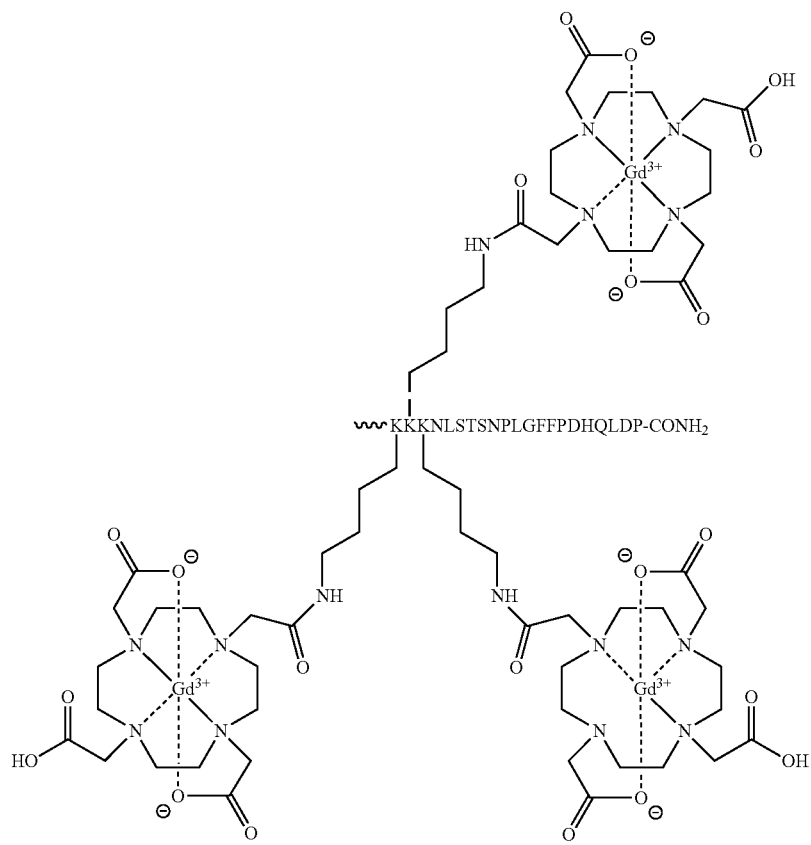

-continued

Stearoyl-[K(DOTA[$^{68}$Ga])]$_3$-NLSTSNPLGFFPDHQLDP-amide

Stearoyl-[K(DOTA[$^{111}$In])]$_3$-NLSTSNPLGFFPDHQLDP-amide

Stearoyl-[K(DOTA[Gd])]$_3$-NLSTSNPLGFFPDHQLPD-amide

Stearoyl-[K(DOTA[$^{68}$Ga])]$_3$-NLSTSNPLGFFPDHQLPD-amide

Stearoyl-[K(DOTA[$^{111}$In])]$_3$-NLSTSNPLGFFPDHQLPD-amide

TABLE 1

Preferred hydrophobic modified peptides

| Hydrophobic modified Peptide | Coupled Label/ Agent | Application |
|---|---|---|
| stearoyl-[K(DOTA[Gd])]$_3$-NLSTSNPLGFFPDHQLDP-amide | Gd | Diagnosis |
| stearoyl-[K(DOTA[$^{68}$Ga])]$_3$-NLSTSNPLGFFPDHQLDP-amide | $^{68}$Ga | Diagnosis |
| stearoyl-[K(DOTA[$^{111}$In])]$_3$-NLSTSNPLGFFPDHQLDP-amide | $^{111}$In | Diagnosis |
| stearoyl-[K(DOTA[Gd])]3-NLSTSNPLGFFPDHQLPD-amide | Gd | Diagnosis |
| stearoyl-[K(DOTA[68Ga])]3-NLSTSNPLGFFPDHQLPD-amide | $^{68}$Ga | Diagnosis |
| stearoyl-[K(DOTA[111In])]3-NLSTSNPLGFFPDHQLPD-amide | $^{111}$In | Diagnosis | stearoyl refers to stearoylation of the N-terminus

The following examples and drawings illustrate the present invention without, however, limiting the same thereto.

BRIEF DESCRIPTION OF THE FIGURES

FIG. 4A Specific enrichment of 400 nmol/kg stearoyl-[K(DOTA[$^{68}$Ga])]$_3$-NLSTSNPLGFFPDHQLDP-amide of SEQ ID NO: 15 in the liver of a WAG/Rji rat five minutes post i.v. injection. FIG. 4B Counterstain using $^{18}$F-FDG 24 hours after the initial measurement $^{18}$F-FDG is enriched in organs consuming high amounts of glucose, in the picture the heart (grey mass on the top) and the tumour enrich glucose ($^{18}$F-FDG enriched in the brain is not shown for technical reasons). FIG. 4C Merge of both images demonstrating the specificity of the peptides staining only liver tissue but not the tumor tissue.

EXAMPLES

Figure 1:
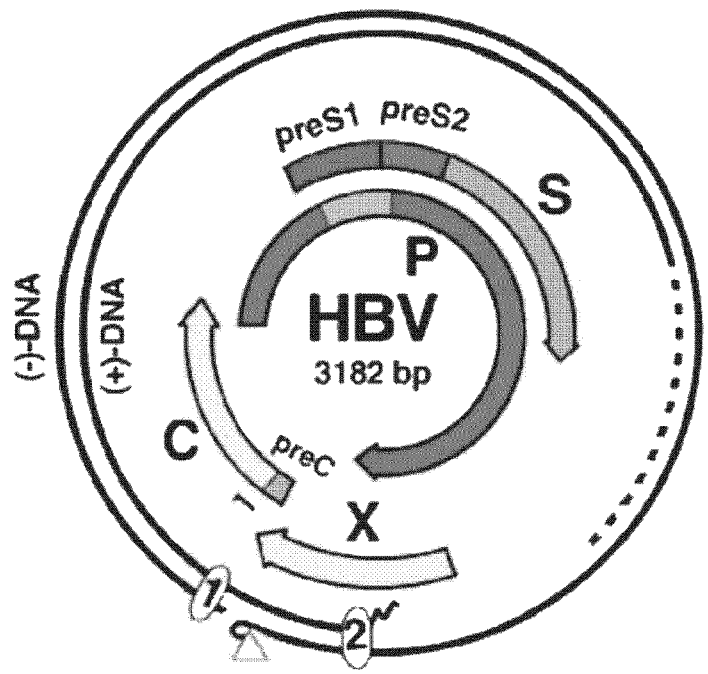
FIG. 1: Schematic representation of the HBV particle and the HBV L-, M- and S-proteins. The partially double stranded DNA is covalently associated with the viral polymerase complex, consisting of the terminal protein, (TP), the reverse transcriptase (RT) and the RNaseH. The genome is encapsulated by an icosahedral shell, built of 120 core-protein dimers. The 3 HBV surface proteins L-, M- and S- are embedded into an ER-derived lipid bilayer. The L- and M-proteins contain the complete S-domain serving as a membrane anchor. Schematic representation of the partially double stranded DNA genome of HBV; C=Core protein forming the viral capsid; X=X Protein, a pleiotropic trans-activator with undefined function; P=Viral Polymerase; preS1/preS2/S combinations of these form the large (preS1/preS2/S) HBV surface protein (L Protein) the medium (preS2/S) HBV surface protein and the small (S) HBV surface protein.
Figure 1:
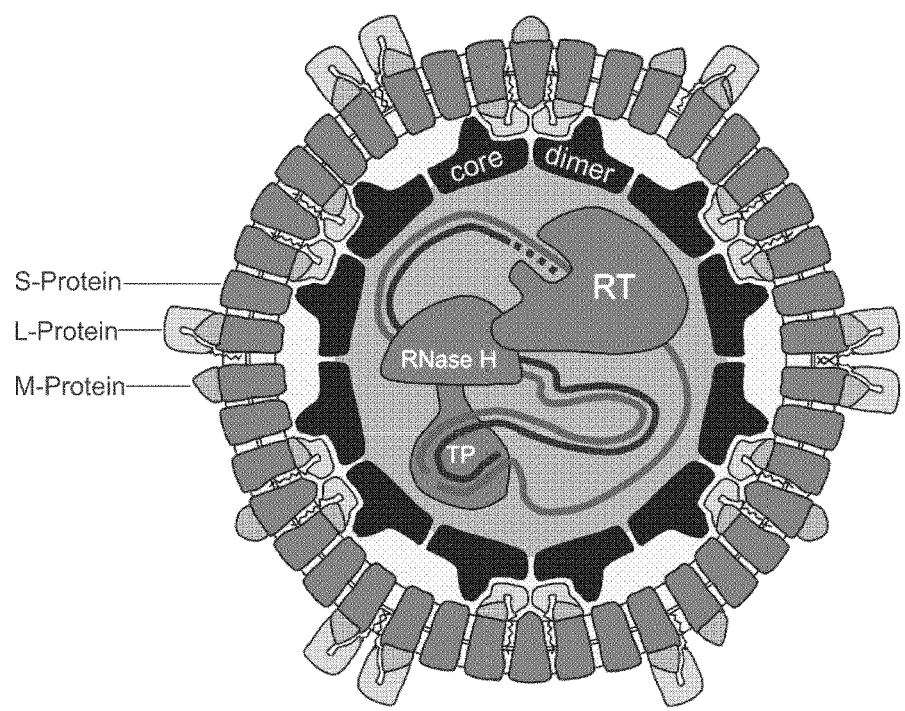
Figure 2:
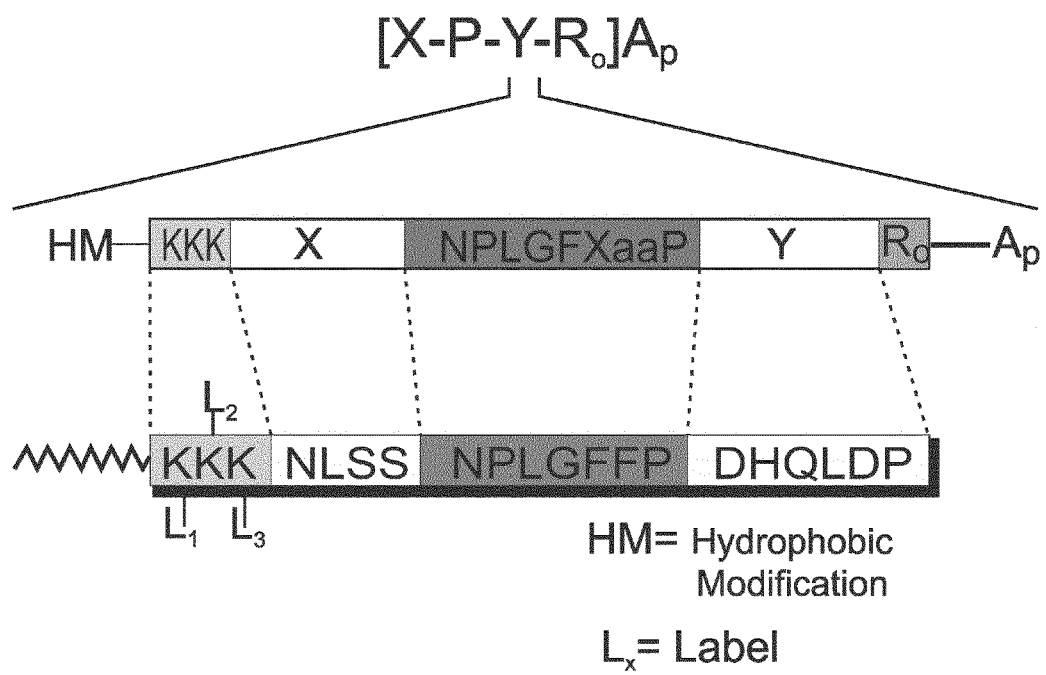
FIG. 2: Schematic diagram of the general formula of SEQ ID NO: 1, the hydrophobic modified peptide of the present invention (i.e., NPLGFXaaP) and an example of SEQ ID NO: 21, a hydrophobic modified peptide of the invention (i.e., KKKNLSSNPLGFFPDHQLDP).
Figure 3:
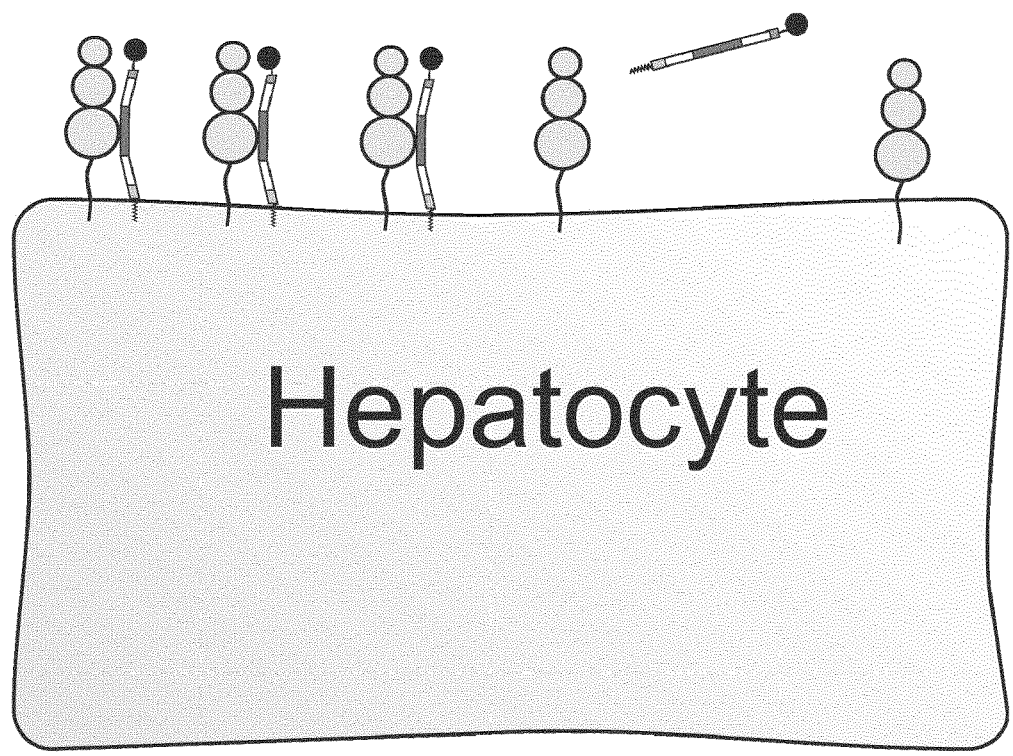
FIG. 3: Schematic diagram of the binding of a hydrophobic modified peptide of the invention to the surface of a hepatocyte.

In the following examples hydrophobic peptides carrying Gd, $^{68}$Ga or $^{111}$In as labels complexed with DOTA (stearoyl-[K(DOTA[Gd])]$_3$-NLSTSNPLGFFPDHQLDP-amide, stearoyl-[K(DOTA[$^{68}$Ga])]$_3$-NLSTSNPLGFFPDHQLDP-amide or stearoyl-[K(DOTA[$^{111}$In])]$_3$-NLSTSNPLGFFPDHQLDP-amide) of SEQ ID NO: 15, were used as exemplary products of the present invention. If not indicated otherwise, the in vivo experiments using different medical imaging methods have been conducted by using WAG/Rij rats.

Example 1

Synthesis of the Hydrophobic Modified Peptide

The synthesis of the peptides was carried out by using the Fmoc method as described in (10) Gripon, P. et al. J Virol 79, 1613-1622 (2005).

Synthesis DOTA-DFP

Diisopropylcarbodiimide (5 mmol, 631 mg, 774 µl) was dissolved in pyridine (15 ml) and dropped over 10 min to a solution of DOTA (5 mmol, 2.02 g) and difluoro phenole (5 mmol, 650 mg) in water (60 ml) while stirring. 30 min after addition, the reaction mixture was extracted three times with dichlormethane and the aqueous phase was evaporated to dryness by using a rotating evaporator. The crude product was dissolved in a mixture of water (11 ml) and acetonitrile (3 ml) and was purified via preparative RP-HPLC. The HPLC fractions containing the product were concentrated by lyophilisation. Yield: 1.0633 g (41%).

Coupling to the Peptide

The peptide stearoyl-KKKNLSTSNPLGFFPDHQLDP-amide or stearoyl-SEQ ID NO: 15-amide (140 mg, 0.055 mmol) was dissolved in 5 ml DMF. DOTA-DFP (129 mg, 0.25 mmol) was added and, furthermore, DIPEA (410 µl, 2.5 mmol) was added. The mixture was stirred over night at 50° C. Diethylether was added until precipitation; the precipitate was separated by using a centrifuge and was washed twice with diethylether. The crude product was purified by using RP-HPLC. The purification was effected by using a gradient of water and acetonitrile, both comprising 0.1% trifluoroacetic acid. The HPLC fractions containing the product were concentrated by lyophilisation. Yield: 112 mg (55%).

Complexing of $Gd^{3+}$

The peptide stearoyl-[K(DOTA)]$_3$-NLSTSNPLGFFPD-HQLDP-amide of SEQ ID NO: 15 (112 mg, 0.030 mmol) was dissolved in 0.4 M sodium acetate buffer (pH 5) and $GdCl_3$*6 $H_2O$ (335 mg, 0.90 mmol) was added. The mixture was heated for 1 h in a water bath while stirring. The resulting mixture of products was purified by using RP-HPLC. The purification was effected by using a gradient of water and acetonitrile, both comprising 0.1% trifluoroacetic acid. The HPLC fractions containing the product (stearoyl-[K(DOTA[Gd])]$_3$-NLSTSNPLGFFPDHQLDP-amide of SEQ ID NO: 15) were concentrated by lyophilisation. Yield: 94 mg (77%).

Example 2

Imaging in PET

Figure 4:
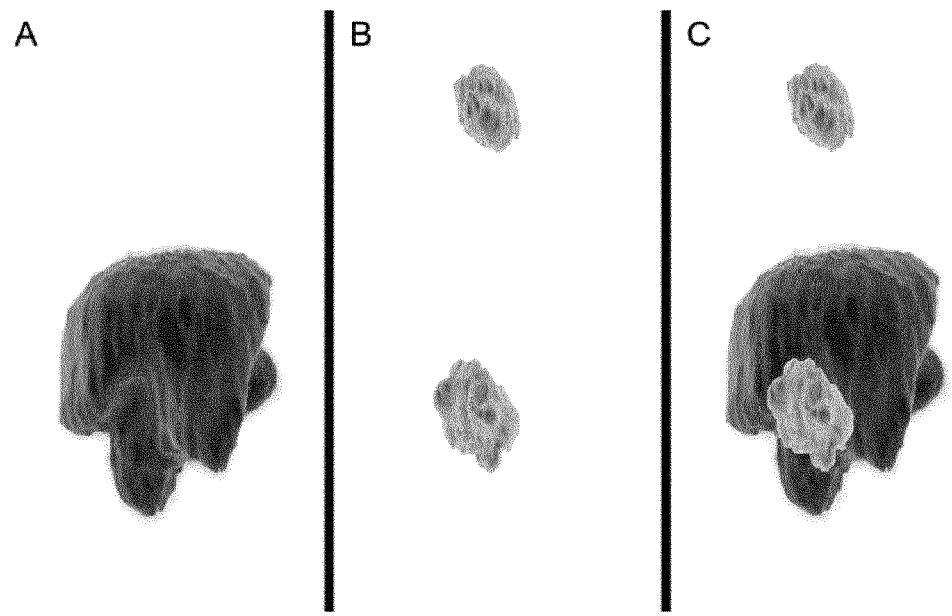
FIG. 4. PET image of a tumor bearing rat.

The peptide stearoyl-[K(DOTA[$^{68}$Ga])]$_3$-NLSTSNPL-GFFPDHQLDP-amide of SEQ ID NO: 15 was dissolved in citrate buffer (pH 8.0)+4% BSA and injected i.v. in the tail vene of tumour bearing rats. The rats were orthopically injected with 1×10$^6$ syngenic colon carcinoma cells (CC531 cells) 10 days prior to the measurements. At the day of measurement the rats received the peptide in a concentration of 400 nmol/kg body weight. During the experiments the rats were anaesthetised by isoflurane and kept at 37° C. PET imaging was performed using a Inveon small animal PET from Siemens, imaging was started immediately after i.v. injection of the peptide 24 h after the initial measurement using stearoyl-[K(DOTA[$^{68}$Ga])]$_3$-NLSTSNPLGFFPD-HQLDP-amide of SEQ ID NO: 15, the rats were injected with $^{18}$F-FDG (Fluodeoxyglucose($^{18}$F) in a concentration of 5 millicuries as a control. FIG. 4A-C shows a representative PET image of a tumor bearing rat. FIG. 4A Specific enrichment of 400 nmol/kg stearoyl-[K(DOTA[$^{68}$Ga])]$_3$-NLST-SNPLGFFPDHQLDP-amide of SEQ ID NO: 15 in the liver of a WAG/Rji rat five minutes post i.v. injection. FIG. 4B Counterstain using $^{18}$F-FDG 24 hours after the initial measurement $^{18}$F-FDG is enriched in organs consuming high amounts of glucose, in the picture the heart (grey mass on the top) and the tumour enrich glucose ($^{18}$F-FDG enriched in the brain is not shown for technical reasons). FIG. 4C Merge of both images demonstrating the specificity of the peptides staining only liver tissue but not the tumor tissue.

Example 3

Imaging in MRI

Figure 5:
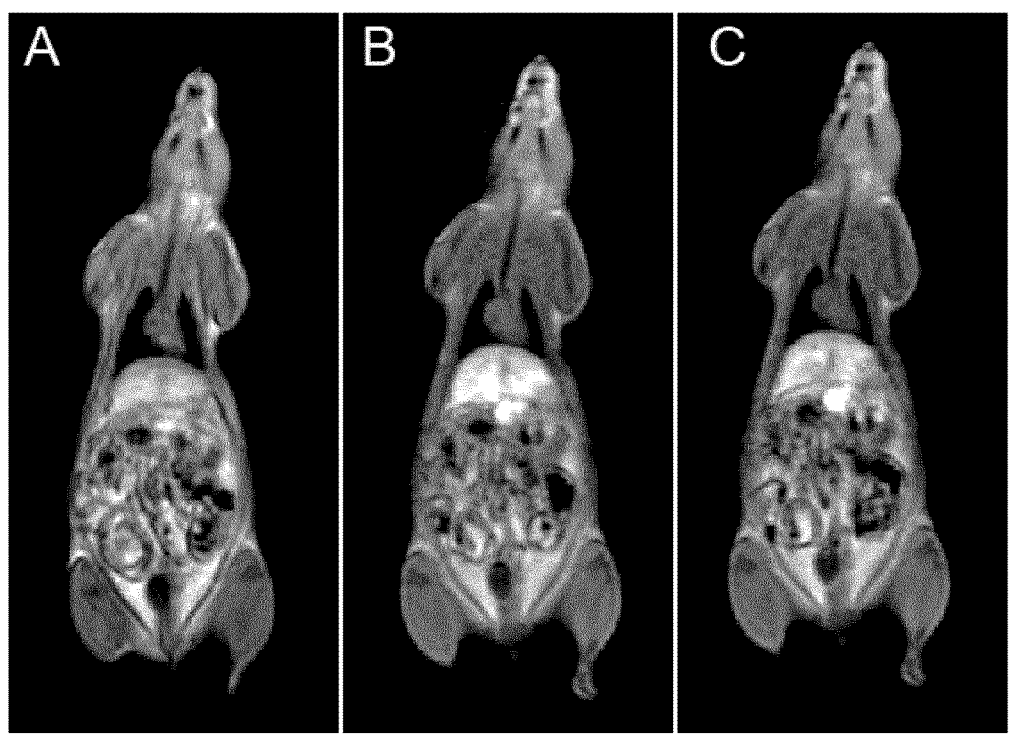
FIG. 5 shows a representative MRI image series of a Rat before injection of 600 nmol/kg body weight stearoyl-[K(DOTA[Gd])]$_3$-NLSTSNPLGFFPDHQLDP of SEQ ID NO: 15 (FIG. 5A) as well as 20 (FIG. 5B) and 30 minutes (FIG. 5C) post injection.

The peptide stearoyl-[K(DOTA[Gd])]$_3$-NLSTSNPLGFF-PDHQLDP-amide of SEQ ID NO: 15 was dissolved in citrate buffer (pH 8.0)+4% BSA and injected i.v. in the tail vene of the rats in a concentration of 600 nmol/kg body weight. During the experiments the rats were anaesthetised by isoflurane. Upon application of the peptide, the rats were examined in MRI with T1 contrast sensitive sequences (Siemens ViBE®). The measurement was conducted on a Siemens Avanto 1.5 T MRI Scanner. FIG. 5 shows a representative image of a healthy rate before, as well as 20 and 30 minutes after i.v. injection.

Example 4

Dose Escalation

Figure 6:
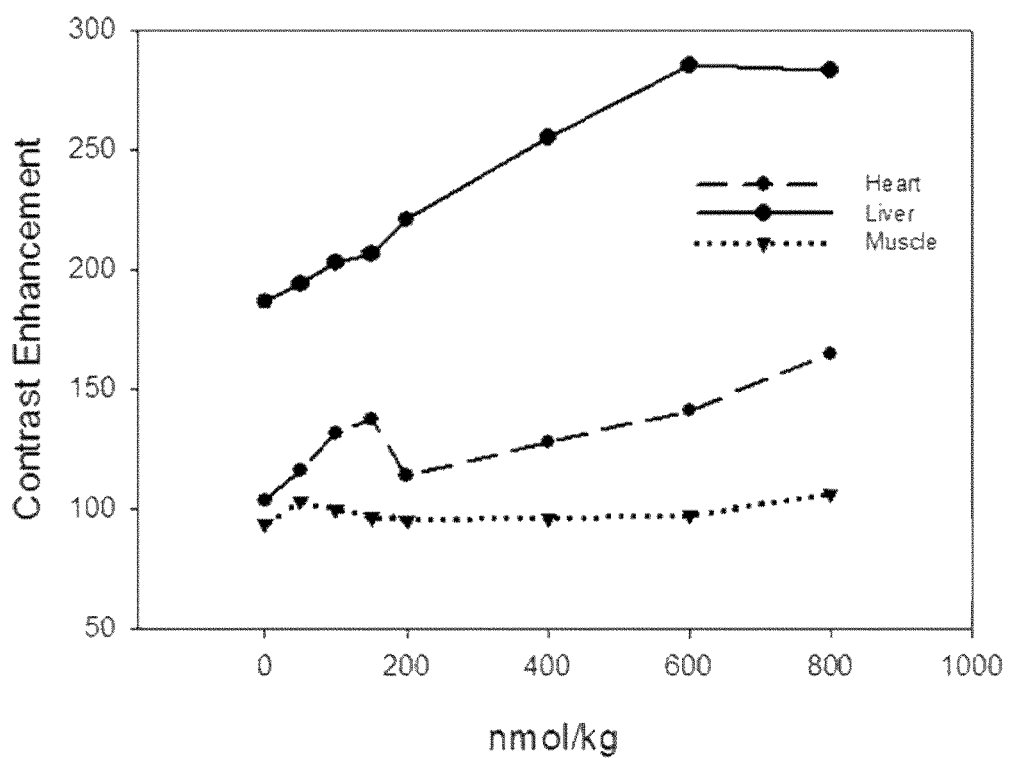
FIG. 6 shows the contrast enhancement determinded by MRI measurement in liver, muscle tissue and heart.

Isoflurane anaesthetised rats received increasing amounts of stearoyl-[K(DOTA[Gd])]$_3$-NLSTSNPLGFFPDHQLDP-amide of SEQ ID NO: 15 in subsequent i.v. injections. The interval between subsequent injections was 20 min. In the time between two injections, continued MRI measurements of the liver with T1 contrast sensitive sequences (Siemens ViBE®) were made and the enhancement of the contrast in liver, muscle tissue and heart was determined. In parallel, contrast values of the clinical relevant dosage of Primovist™ were determined. The result is shown in FIG. 6.

Example 5

Determining the R1/R2 Relaxivity by NMR

Figure 7:
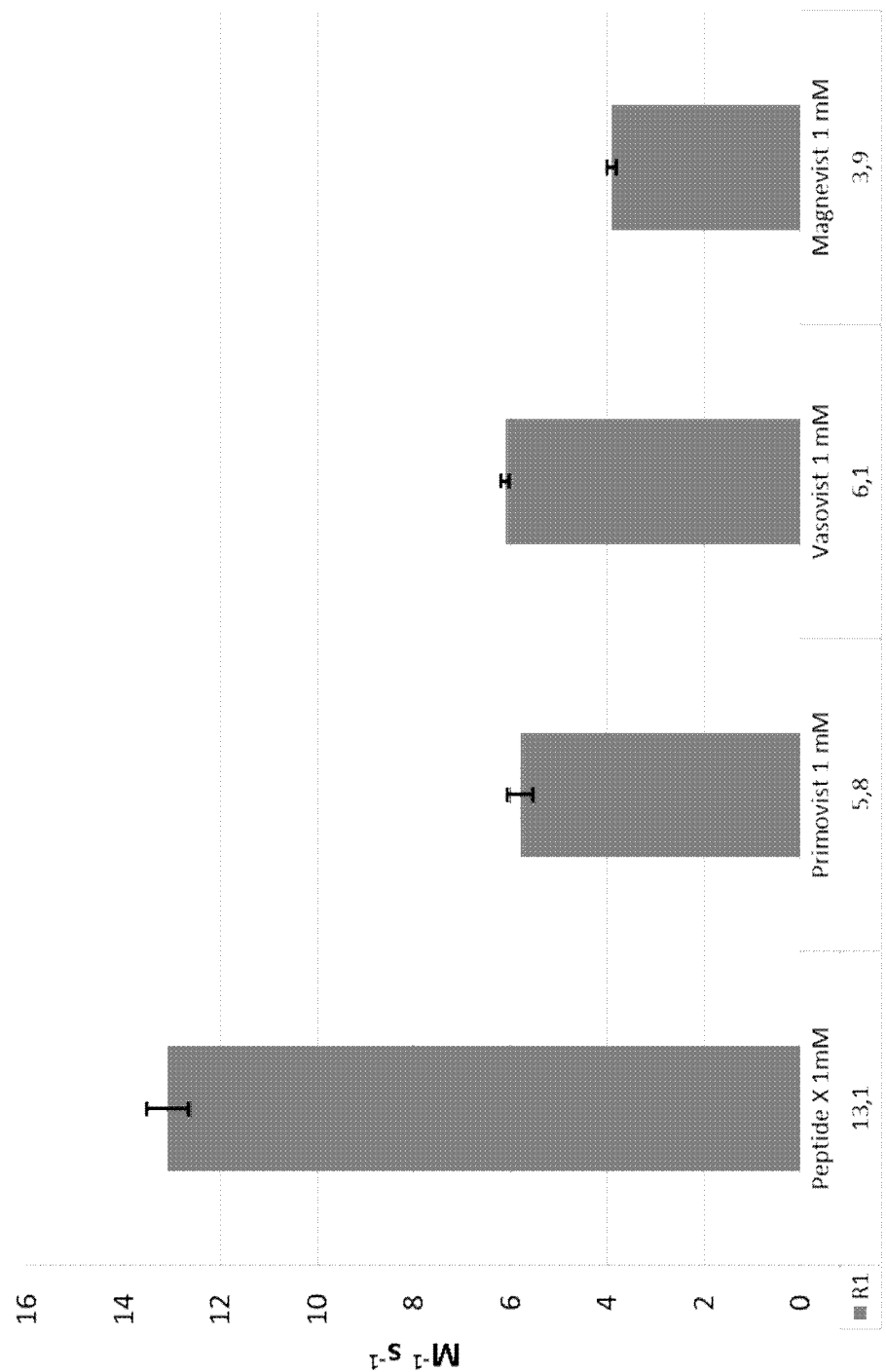
FIG. 7: R1 relaxivity of the peptide stearoyl-[K(DOTA[Gd])]$_3$-NLSTSNPLGFFPDHQLDP of SEQ ID NO: 15 (Peptide X), Primovist™, Magnevist™ and Vasovist™ dissolved in PBS in equimolar amounts (1 mM).
Figure 8:
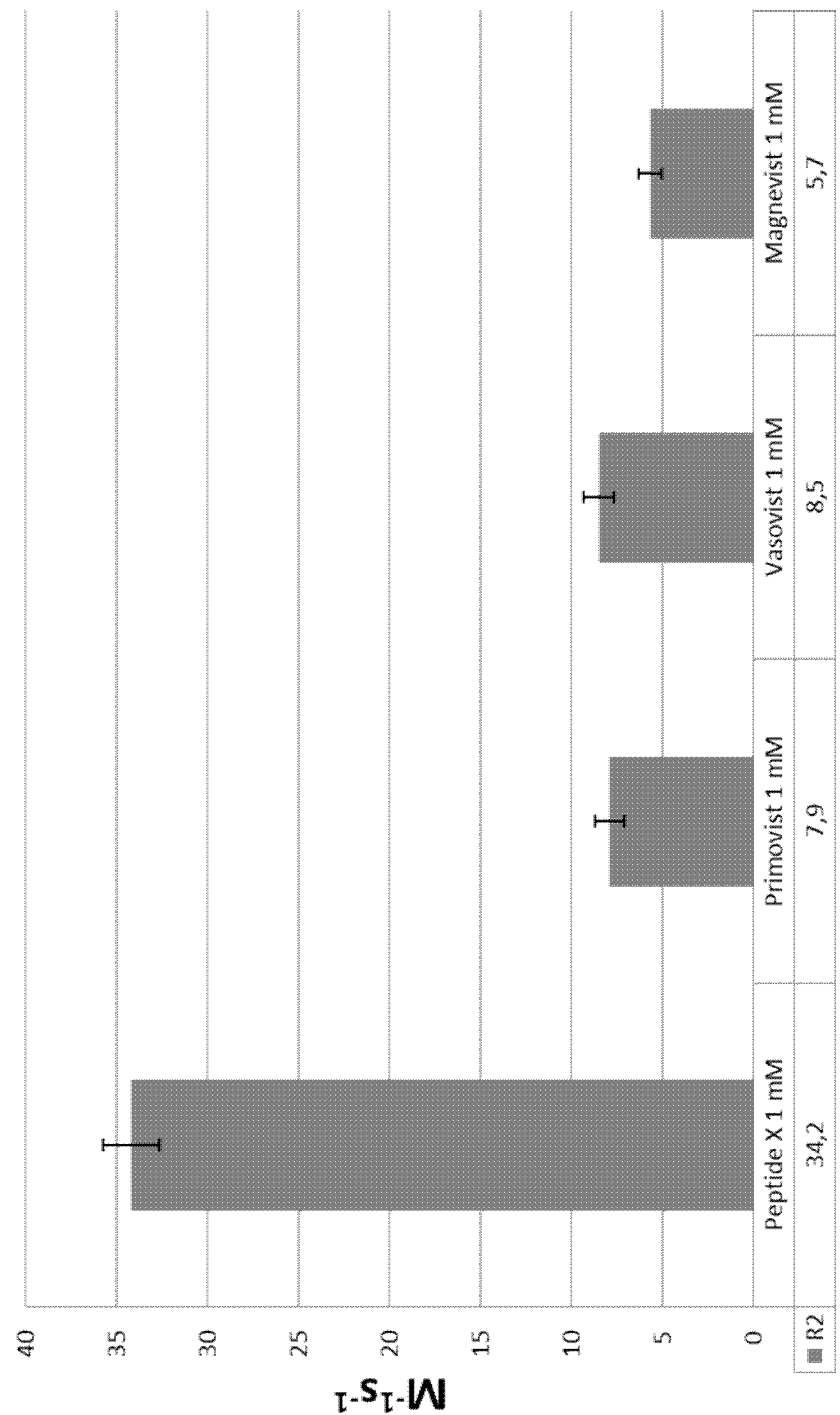
FIG. 8: R2 realxivity of the peptide stearoyl-[K(DOTA[Gd])]$_3$-NLSTSNPLGFFPDHQLDP of SEQ ID NO: 15 (Peptide X), Primovist™, Magnevist™ and Vasovist™ dissolved in PBS in equimolar amounts (1 mM).

The peptide stearoyl-[K(DOTA[Gd])]$_3$-NLSTSNPLGFF-PDHQLDP of SEQ ID NO: 15 ("Peptide X"; 1 mM), Primovist™ (1 mM), Magnevist™ (1 mM) as well as Vasovist™ (1 mM) were dissolved in PBS in equimolar amounts at room temperature and the R1/r2 relaxivities were measured in a Varian 300 Mhz NMR. By using Fourier transformation, the single contrast values were determined from the data resulting from the experiment. The results are shown in FIG. 7 and FIG. 8.

Example 6

Organ Distribution Studies

Figure 9:
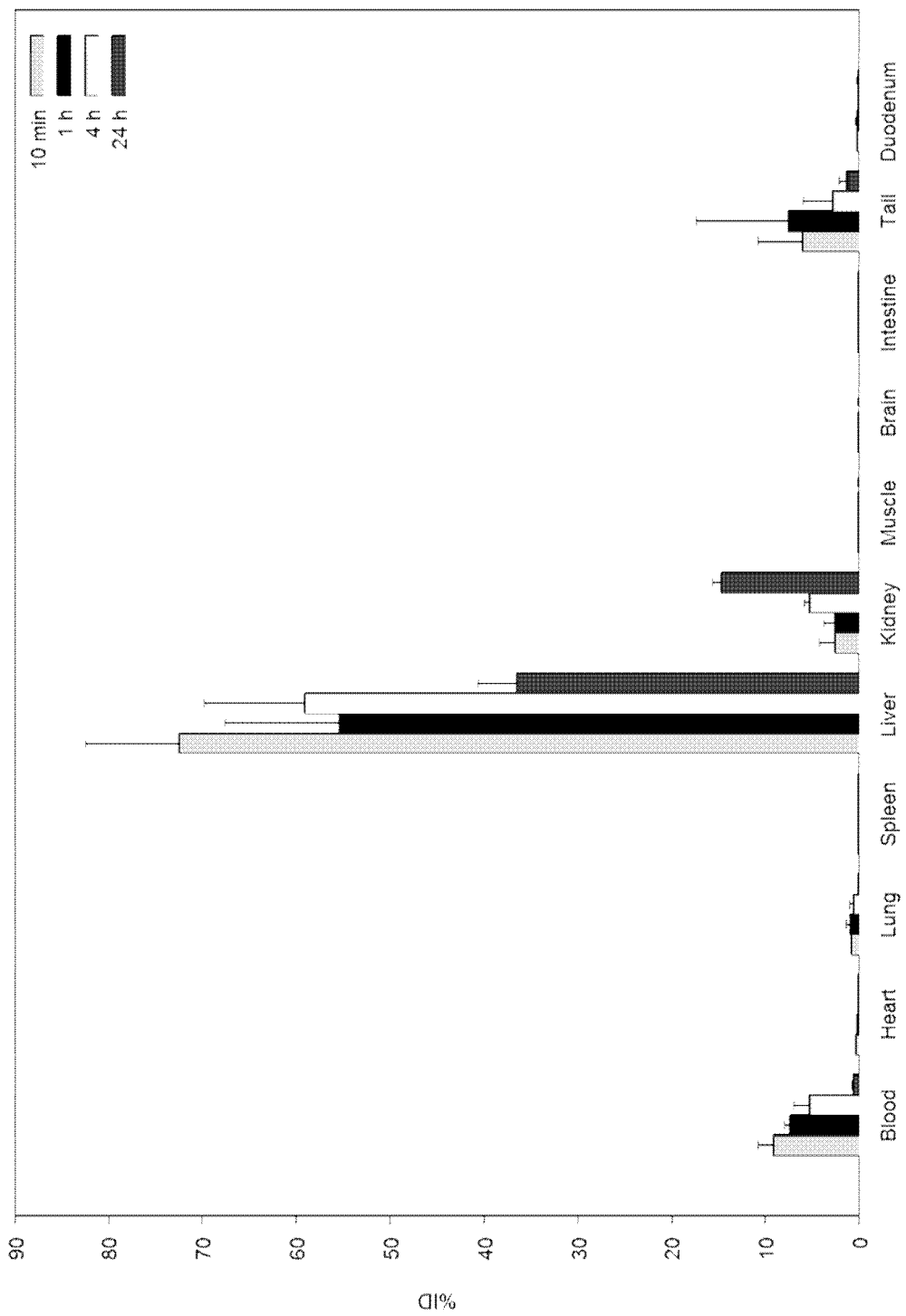
FIG. 9: Organ distribution of $^{111}$In labelled hydrophobic modified peptide in mice.

For examining the organ distribution $^{111}$In labelled peptide stearoyl-[K($^{111}$In DOTA)]$_3$-NLSTSNPLGFFPD-HQLDP of SEQ ID NO: 15 was dissolved in citrate buffer (pH 8.0)+4% BSA and injected i.v. in the tail vene of mice in a concentration of 400 nmol/kg body weight. The mice were euthanized at the given time points and blood and organs were taken. The radioactive signal of each organ was determined by using a Gamma-Counter. The results are shown in FIG. 9.

Example 7

Stability in the Serum

Figure 10:
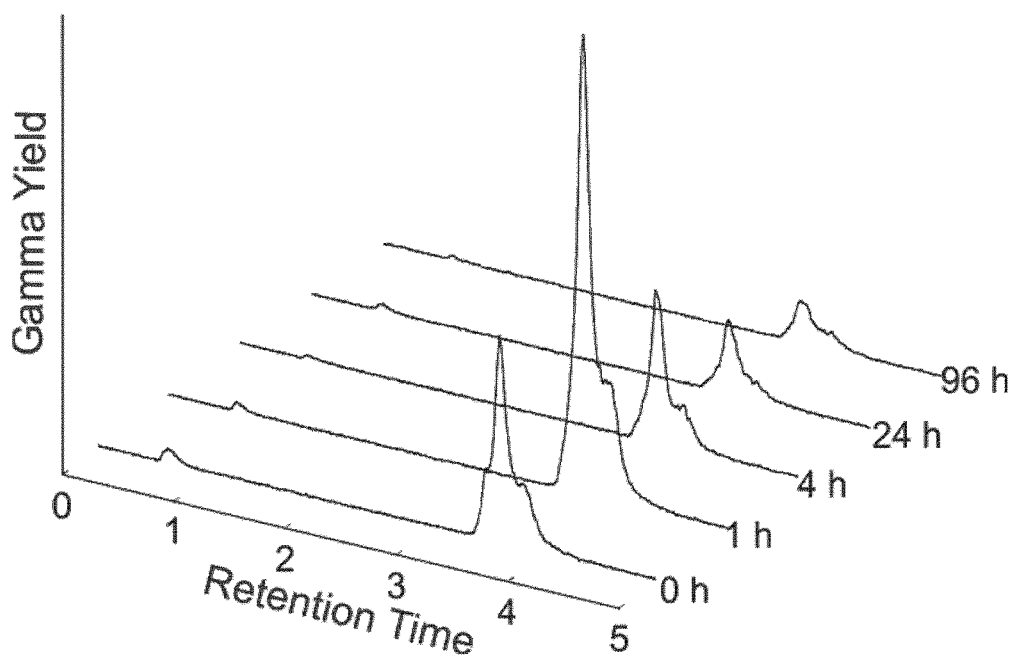
FIG. 10: Stability of stearoyl-[K(DOTA[$^{68}$Ga])]$_3$-NLSTSNPLGFFPDHQLDP-amide of SEQ ID NO: 15 in non-inactivated human serum.

Stearoyl-[K(DOTA[$^{68}$Ga])]$_3$-NLSTSNPLGFFPD-HQLDP-amide of SEQ ID NO: 15 was incubated at 37° C. in non-inactivated human serum from healthy voluntary donors over the indicated period. The detection of degradation products was conducted by purification of the peptides by using HPLC affinity chromatography and subsequent radioactivity determination was performed on a gamma counter at the indicated time points. The correct mass of the radioactive peak fractions eluted from the column was confirmed by mass spectrometry (data not shown). The results are shown in FIG. 10. Only radioactive decay but no cleavage was observed.

The features disclosed in the foregoing description, in the claims and/or in the accompanying drawings may, both separately and in any combination thereof, be material for realizing the invention in diverse forms thereof.

REFERENCES

1. Seeger, C. & Mason, W. S. Hepatitis B virus biology. Microbiol MoI Biol Rev 64, 51-68 (2000).
2. Nassal, M. Hepatitis B virus morphogenesis. Curr Top Microbiol Immunol 214, 297-337 (1996).
3. Gripon, P., Le Seyec, J., Rumin, S. & Guguen-Guillouzo, C. Myristylation of the hepatitis B virus large surface protein is essential for viral infectivity. Virology 213, 292-299 (1995).
4. Le Seyec, J., Chouteau, P., Cannie, L, Guguen-Guillouzo, C. & Gripon, P. Infection process of the hepatitis B virus depends on the presence of a defined sequence in the pre-S1 domain. J Virol 73, 2052-2057 (1999).
5. Juliano R L (1988) Factors affecting the clearance kinetics and tissue distribution of liposomes, microspheres, and emulsions. Adv Drug Deliv Rev 2: 31-54.
6. Hashida M and Takakura Y (1994) Pharmacokinetics in design of polymeric drug delivery systems. J Control Release 31: 163-171.
7. Lu, X. M., Fischman, A. J., Jyawook, S. L., Hendricks, K., Tompkins, R. G. and Yarmush, M. L. (1994) Antisense DNA delivery in vivo: liver targeting by receptor-mediated uptake. J. Nucl. Med. 35, 269-275.
8. Kasuya T, Kuroda S. Nanoparticles for human liver-specific drug and gene delivery systems: in vitro and in vivo advances. Expert Opin Drug Deliv. 2009 January; 6(1):39-52. Review. PubMed PMID: 19236207.
9. Yamada T, Iwasaki Y, Tada H, Iwabuki H, Chuah M K, VandenDriessche T, Fukuda H, Kondo A, Ueda M, Seno M, Tanizawa K, Kuroda S. Nanoparticles for the delivery of genes and drugs to human hepatocytes. Nat Biotechnol. 2003 August; 21(8):885-90. Epub 2003 Jun. 29. PubMed PMID: 12833071
10. Gripon, P., Cannie, I. & Urban, S. Efficient inhibition of hepatitis B virus infection by acylated peptides derived from the large viral surface protein. J Virol 79, 1613-1622 (2005).
11. (1998). "A new prognostic system for hepatocellular carcinoma: a retrospective study of 435 patients: the Cancer of the Liver Italian Program (CLIP) investigators." Hepatology 28(3): 751-755.
12. Bruix, J. and M. Sherman (2005). "Management of hepatocellular carcinoma." Hepatology 42(5): 1208-1236.
13. Llovet, J. M., J. Bustamante, et al. (1999). "Natural history of untreated nonsurgical hepatocellular carcinoma: rationale for the design and evaluation of therapeutic trials." Hepatology 29(1): 62-67.
14. Gogel, B. M., R. M. Goldstein, et al. (2000). "Diagnostic evaluation of hepatocellular carcinoma in a cirrhotic liver." Oncology (Williston Park) 14(6 Suppl 3): 15-20.
15. Fearon, E. R. & Vogelstein, B. A genetic model for colorectal tumorigenesis. Cell 61, 759-767 (1990).
16. Winawer, S. J., et al. Colorectal cancer screening: clinical guidelines and rationale. Gastroenterology 112, 594-642 (1997).
17. Johnson, F. E., et al. How tumor stage affects surgeons' surveillance strategies after colon cancer surgery. Cancer 76, 1325-1329 (1995).
18. Johnson, F. E., et al. Geographic variation in patient surveillance after colon cancer surgery. J Clin Oncol 14, 183-187 (1996).
19. Johnson, F. E., et al. How practice patterns in colon cancer patient follow-up are affected by surgeon age. Surg Oncol 5, 127-131 (1996).
20. Vernava, A. M., 3rd, et al. Current follow-up strategies after resection of colon cancer. Results of a survey of members of the American Society of Colon and Rectal Surgeons. Dis Colon Rectum 37, 573-583 (1994).
21. Virgo, K. S., et al. Surveillance after curative colon cancer resection: practice patterns of surgical subspecialists. Ann Surg Oncol 2, 472-482 (1995).
22. Khatri, V. P., Petrelli, N. J. & Belghiti, J. Extending the frontiers of surgical therapy for hepatic colorectal metastases: is there a limit? J Clin Oncol 23, 8490-8499 (2005).

The invention claimed is:

1. A hydrophobic modified peptide of the formula

[X—P—Y—R$_o$]A$_p$, wherein
   X is an amino acid sequence having a length of m amino acids,
   wherein m is at least 4, and
   wherein the N-terminus of X comprises one or more amino acids comprising an amino group in the side chain,
   wherein the one or more of the amino acids comprising an amino group in the side chain comprises a hydrophobic modification selected from acylation with carboxylic acids, fatty acids, and amino acids with lipophilic side chains or addition of a hydrophobic moiety selected from the group consisting of cholesterol, derivatives of cholesterol, a phospholipid, a glycolipid, a glycerol ester, steroids, a ceramide, an isoprene derivative, adamantane, farnesol, an aliphatic group, and a polyaromatic compound; and
   wherein the one or more amino acids comprising the amino group in the side chain is coupled to one or more labels selected from the group consisting of a fluorescent dye, a fluorescence emitting isotope, a radioisotope, and a contrast agent
   P is a peptide comprising the amino acid sequence NPL-GFXaaP (SEQ ID NO: 1), wherein Xaa is an arbitrary amino acid;
   Y is an amino acid sequence having a length of n amino acids, wherein n is 0 or at least 1;

$m+n \geq 11$

R is a C-terminal modification of said hydrophobic modified peptide, which protects from degradation selected from the group consisting of an amide, a D-amino acid, a modified amino acid, a cyclic amino acid, an albumin, a natural polymer, a synthetic polymer, and a glycane;
   o is 0 or at least 1; and
   A is an anchor group selected from the group consisting of an ester, an ether, a disulfide, an amide, a thiol, and a thioester; p is 0 or at least 1.

2. The hydrophobic modified peptide according to claim 1, wherein m is 4 to 10 and/or n is 0 to 78.

3. The hydrophobic modified peptide according to claim 1, wherein Xaa is F or L.

4. The hydrophobic modified peptide according to claim 3, wherein Xaa is F.

5. The hydrophobic modified peptide according to claim 1, wherein the one or more amino acids is coupled to a label via a linker or spacer.

6. The hydrophobic modified peptide according to claim 5, wherein the linker or spacer is cleaved by a liver protein.

7. The hydrophobic modified peptide according to claim 6, wherein the linker or spacer is cleaved by an enzyme selected from a cytochrome, a protease of the endocytic pathway, a lyase of the endocytic pathway, matrix-metallo-protease 1 (MMP1), matrix-metallo-protease 2 (MMP2), matrix-metallo-protease 7 (MMP7), matrix-metallo-protease 9 (MMP9), and matrix-metallo-protease 12 (MMP12).

8. The hydrophobic modified peptide according to claim 7, wherein the linker or spacer comprises the amino acid sequence selected from GCHAK (SEQ ID NO: 19) and RPLALWRS (SEQ ID NO: 20).

9. The hydrophobic modified peptide according to claim 1, wherein the one or more amino acids of X comprising the amino group in the side chain is selected from the group consisting of lysine, α-amino glycine, α,γ-diaminobutyric acid, ornithine, and α,β-diaminopropionic acid.

10. The hydrophobic modified peptide according to claim 1, wherein the N-terminus comprises 2 to 11 amino acids comprising an amino group in the side chain.

11. The hydrophobic modified peptide according to claim 10, wherein the one or more amino acids of X comprising the amino group in the side chain is coupled to the label via an activated ester.

12. The hydrophobic modified peptide according to claim 10, wherein the N-terminus of X comprises 1 to 3 amino acids having an amino group in a side chain.

13. The hydrophobic modified peptide according to claim 1, wherein the one or more labels are coupled to the amino acids of X comprising the amino group in the side chain by using one or more methods selected from
   formation of amides by the reaction of an amine and activated carboxylic acids, NHS-esters, or carbodiimides;
   disulfide linkage using two thiols or one thiol that specifically reacts with pyridyl disulfides;
   thioether formation using maleimides or haloacetyls and a thiol component;
   amidine formation using an imidoester and an amine;
   hydrazide linkage using carbonyls and hydrazides;
   amine linkage using carbonyls and amines under reductive conditions;
   triazol formation using nitriles and azides;
   thiourea formation using isothiocyanates and amines;
   formation of esters by the reaction of an alcohol and activated carboxylic acids, acid chlorides, or carbodiimides; and
   formation of ethers by the reaction of an alcohol and alkyl halides.

14. The hydrophobic modified peptide according to claim 13, wherein the carbonyls used in the hydrazide linkage are aldehydes.

15. The hydrophobic modified peptide according to claim 1, wherein the hydrophobic modification is by acylation selected from acylation with myristoyl (C14), palmitoyl (C16) or stearoyl (C18).

16. The hydrophobic modified peptide according to claim 15, wherein the hydrophobic modification is by acylation with myristoyl (C14).

17. The hydrophobic modified peptide according to claim 15, wherein the hydrophobic modification is by acylation with stearoyl (C18).

18. The hydrophobic modified peptide according to claim 1, wherein the label comprises a chelating agent selected from the group consisting of 1,4,7,10-tetraazacyclododecane-N,N',N,N'-tetraacetic acid (DOTA), ethylenediaminetetraacetic acid (EDTA), 1,4,7-triazacyclononane-1,4,7-triacetic acid (NOTA), triethylenetetramine (TETA), iminodiacetic acid, Diethylenetriamine-N,N,N',N',N''-pentaacetic acid (DTPA) and 6-Hydrazinopyridine-3-carboxylic acid (HYNIC).

19. The hydrophobic modified peptide according to claim 18, wherein the chelating agent is 1,4,7,10-tetraazacyclododecane-N,N',N,N'-tetraacetic acid (DOTA).

20. The hydrophobic modified peptide according to claim 1, wherein
(a) the contrast agent comprises a paramagnetic agent;
(b) the radioisotope/fluorescence emitting isotope is selected from the group consisting of alpha radiation emitting isotopes, gamma radiation emitting isotopes, Auger electron emitting isotopes, X-ray emitting isotopes, and fluorescence emitting isotopes; and
(c) the fluorescent dye is selected from the group consisting of the following classes of fluorescent dyes: xanthens, acridines, oxazines, cynines, styryl dyes, coumarins, porphines, metal-ligand-complexes, fluorescent proteins, nanocrystals, perylenes, phtalocyanines, conjugates thereof and combinations thereof.

21. The hydrophobic modified peptide according to claim 20, wherein the radioisotope/fluorescence emitting isotope is selected from the group consisting of $^{18}$F, $^{51}$Cr, $^{67}$Ga, $^{68}$Ga, $^{111}$In, $^{99m}$Tc, $^{140}$La, $^{175}$Yb, $^{153}$Sm, $^{166}$Ho, $^{88}$Y, $^{90}$Y, $^{149}$Pm, $^{177}$Lu, $^{47}$Sc, $^{142}$Pr, $^{159}$Gd, $^{212}$Bi, $^{72}$As, $^{72}$Se, $^{109}$Pd, $^{105}$Rh, $^{101m15}$Rh, $^{119}$Sb, $^{128}$Ba, $^{123}$I, $^{124}$I, $^{131}$I, $^{197}$Hg, $^{211}$At, $^{169}$Eu, $^{203}$Pb, $^{212}$Pb, $^{64}$Cu, $^{67}$Cu, $^{188}$Re, $^{186}$Re, $^{198}$Au and $^{199}$Ag.

22. The hydrophobic modified peptide according claim 1, wherein the hydrophobic modified peptide is selected from the group consisting of:

stearoyl-[K(DOTA[Gd])]₃-NLSTSNPLGFFPDHQLDP, (SEQ ID NO: 15)

stearoyl-[K(DOTA[$^{68}$Ga])]₃-NLSTSNPLGFFPDHQLDP, (SEQ ID NO: 15)

stearoyl-[K(DOTA[$^{111}$In])]₃-NLSTSNPLGFFPDHQLDP, (SEQ ID NO: 15)

stearoyl-[K(DOTA[Gd])]₃-NLSTSNPLGFFPDHQLDP)-amide, (SEQ ID NO: 15)

stearoyl-[K(DOTA[$^{68}$Ga])]₃-NLSTSNPLGFFPDHQLDP-amide, (SEQ ID NO: 15)
and stearoyl-[K(DOTA[$^{111}$In])]₃-NLSTSNPLGFFPDHQLDP-amide. (SEQ ID NO: 15)

23. The hydrophobic modified peptide according to claim 1, wherein the hydrophobic modification is by acylation with carboxylic acid.

24. The hydrophobic modified peptide according to claim 1, wherein the fatty acids are $C_8$ to $C_{22}$ fatty acids.

25. The hydrophobic modified peptide according to claim 1, wherein the synthetic polymer is PEG.

26. A pharmaceutical composition comprising: at least one hydrophobic modified peptide according to claim 1; and,
optionally a pharmaceutically acceptable carrier and/or excipient.

27. A method of specifically delivering a label to the liver by administering to a patient the hydrophobic modified peptide according to claim 1 or a pharmaceutical composition comprising said peptide.

28. The method according to claim 27, wherein the hydrophobic modified peptide is administered to the patient in a dosage ranging from 10 pmol per kg body weight to 20 μmol per kg body weight.

29. The method according to claim 28, wherein the hydrophobic modified peptide is administered to the patient in the dosage ranging from 100 nmol per kg body weight to 2 μmol per kg body weight.

30. The method according to claim 27, wherein the hydrophobic modified peptide is administered to the patient subcutaneously, intravenously, orally, nasally, intramuscularly, transdermally, by inhalation or by suppository.

31. A method of medical imaging comprising
administering to a patient the hydrophobic modified peptide according to claim 1 or a pharmaceutical composition comprising said peptide and
conducting a medical imaging method selected from the group consisting of X-ray, magnetic resonance imaging (MRI), positron emission tomography (PET), single photon emission computed tomography (SPECT), X-ray computed tomography (CT) and combinations thereof.

32. The method according to claim 31, wherein the hydrophobic modified peptide is administered to the patient in a dosage ranging from 10 pmol per kg body weight to 20 μmol per kg body weight.

33. The method according to claim 31, wherein the hydrophobic modified peptide is administered to the patient subcutaneously, intravenously, orally, nasally, intramuscularly, transdermally, by inhalation or by suppository.

34. A method of intraoperative visualization comprising administering to a patient the hydrophobic modified peptide according to claim 1 or a pharmaceutical composition comprising said peptide.

35. The method according to claim 34, wherein the hydrophobic modified peptide is administered to the patient in a dosage ranging from 10 pmol per kg body weight to 20 pmol per kg body weight.

36. The method according to claim 34, wherein the hydrophobic modified peptide is administered to the patient subcutaneously, intravenously, orally, nasally, intramuscularly, transdermally, by inhalation or by suppository.

37. A method of diagnosing or monitoring the treatment of a liver disease or disorder comprising administering to a patient the hydrophobic modified peptide according to claim 1 or a pharmaceutical composition comprising said peptide.

38. The method according to claim 37, wherein the liver disease or disorder is selected from hepatitis, cirrhosis, haemochromatosis,
a disease which involves a liver stadium of a virus or a non-viral pathogen,
a tropical disease, malaria, schistosomiasis, leishmaniasis,
a liver tumor,
liver metastases,
and a metabolic disease.

39. The method according to claim 37, wherein the hydrophobic modified peptide is administered to the patient in a dosage ranging from 10 pmol per kg body weight to 20 pmol per kg body weight.

40. The method according to claim 37, wherein the hydrophobic modified peptide is administered to the patient subcutaneously, intravenously, orally, nasally, intramuscularly, transdermally, by inhalation or by suppository.

* * * * *

SEQUENCE LISTING

```
<160> NUMBER OF SEQ ID NOS: 23

<210> SEQ ID NO 1
<211> LENGTH: 7
<212> TYPE: PRT
<213> ORGANISM: Hepatitis B virus
<220> FEATURE:
<221> NAME/KEY: VARIANT
<222> LOCATION: (6)..(6)
<223> OTHER INFORMATION: Arbitrary amino acid, preferably F or L, more
      preferably F

<400> SEQUENCE: 1

Asn Pro Leu Gly Phe Xaa Pro
1               5

<210> SEQ ID NO 2
<211> LENGTH: 119
<212> TYPE: PRT
<213> ORGANISM: Hepatitis B virus

<400> SEQUENCE: 2

Met Gly Gly Trp Ser Ser Lys Pro Arg Lys Gly Met Gly Thr Asn Leu
1               5                   10                  15
```

```
Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Gln Ala Asn Gln Val Gly Val Gly Ala Phe Gly
 50                  55                  60

Pro Gly Phe Thr Pro Pro His Gly Gly Val Leu Gly Trp Ser Pro Gln
 65                  70                  75                  80

Ala Gln Gly Ile Leu Ala Thr Val Pro Ala Met Pro Pro Pro Ala Ser
            85                  90                  95

Thr Asn Arg Gln Ser Gly Arg Gln Pro Thr Pro Ile Ser Pro Pro Leu
            100                 105                 110

Arg Asp Ser His Pro Gln Ala
            115

<210> SEQ ID NO 3
<211> LENGTH: 119
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
 1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
 50                  55                  60

Pro Gly Phe Thr Pro Pro His Gly Gly Leu Leu Gly Trp Ser Pro Gln
 65                  70                  75                  80

Ala Gln Gly Ile Leu Thr Ser Val Pro Ala Ala Pro Pro Pro Ala Ser
            85                  90                  95

Thr Asn Arg Gln Ser Gly Arg Gln Pro Thr Pro Leu Ser Pro Pro Leu
            100                 105                 110

Arg Asp Thr His Pro Gln Ala
            115

<210> SEQ ID NO 4
<211> LENGTH: 119
<212> TYPE: PRT
<213> ORGANISM: Hepatitis B virus

<400> SEQUENCE: 4

Met Gly Gly Trp Ser Ser Lys Pro Arg Lys Gly Met Gly Thr Asn Leu
 1               5                   10                  15

Ser Val Pro Asn Pro Leu Gly Phe Phe Pro Asp His Gln Leu Asp Pro
            20                  25                  30

Ala Phe Lys Ala Asn Ser Glu Asn Pro Asp Trp Asp Leu Asn Pro His
        35                  40                  45

Lys Asp Asn Trp Pro Asp Ala His Lys Val Gly Val Gly Ala Phe Gly
 50                  55                  60

Pro Gly Phe Thr Pro Pro His Gly Gly Leu Leu Gly Trp Ser Pro Gln
 65                  70                  75                  80

Ala Gln Gly Ile Leu Thr Ser Val Pro Ala Ala Pro Pro Pro Ala Ser
            85                  90                  95
```

```
Thr Asn Arg Gln Ser Gly Arg Gln Pro Thr Pro Leu Ser Pro Pro Leu
                100                 105                 110

Arg Asp Thr His Pro Gln Ala
        115
```

<210> SEQ ID NO 5
<211> LENGTH: 108
<212> TYPE: PRT
<213> ORGANISM: Hepatitis B virus

<400> SEQUENCE: 5

```
Met Gly Gln Asn Leu Ser Thr Ser Asn Pro Leu Gly Phe Phe Pro Glu
1               5                   10                  15

His Gln Leu Asp Pro Ala Phe Lys Ala Asn Thr Asn Asn Pro Asp Trp
            20                  25                  30

Asp Phe Asn Pro Lys Lys Asp Tyr Trp Pro Glu Ala Asn Lys Val Gly
        35                  40                  45

Ala Gly Ala Phe Gly Pro Gly Phe Thr Pro Pro His Gly Gly Leu Leu
    50                  55                  60

Gly Trp Ser Pro Gln Ala Gln Gly Ile Leu Thr Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asp Thr His Pro Gln Ala
                100                 105
```

<210> SEQ ID NO 6
<211> LENGTH: 108
<212> TYPE: PRT
<213> ORGANISM: Hepatitis B virus

<400> SEQUENCE: 6

```
Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Asn Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Met Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Thr Thr His Pro Gln Ala
                100                 105
```

<210> SEQ ID NO 7
<211> LENGTH: 118
<212> TYPE: PRT
<213> ORGANISM: Hepatitis B virus

<400> SEQUENCE: 7

```
Met Gly Leu Ser Trp Thr Val Pro Leu Glu Trp Gly Lys Asn Ile Ser
1               5                   10                  15

Thr Thr Asn Pro Leu Gly Phe Phe Pro Asp His Gln Leu Asp Pro Ala
            20                  25                  30

Phe Arg Ala Asn Thr Arg Asn Pro Asp Trp Asp His Asn Pro Asn Lys
```

```
                35                  40                  45

Asp His Trp Thr Glu Ala Asn Lys Val Gly Val Gly Ala Phe Gly Pro
        50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asp Pro Pro Ala Ser Thr
                85                  90                  95

Asn Arg Gln Ser Gly Arg Gln Pro Thr Pro Ile Thr Pro Leu Arg
                100                 105                 110

Asp Thr His Pro Gln Ala
        115

<210> SEQ ID NO 8
<211> LENGTH: 119
<212> TYPE: PRT
<213> ORGANISM: Hepatitis B virus

<400> SEQUENCE: 8

Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
                20                  25                  30

Leu Phe Arg Ala Asn Ser Ser Ser Pro Asp Trp Asp Phe Asn Thr Asn
                35                  40                  45

Lys Asp Ser Trp Pro Met Ala Asn Lys Val Gly Val Gly Gly Tyr Gly
        50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
                85                  90                  95

Thr Asn Arg Arg Ser Gly Arg Lys Pro Thr Pro Val Ser Pro Pro Leu
                100                 105                 110

Arg Asp Thr His Pro Gln Ala
        115

<210> SEQ ID NO 9
<211> LENGTH: 118
<212> TYPE: PRT
<213> ORGANISM: Hepatitis B virus

<400> SEQUENCE: 9

Met Gly Leu Ser Trp Thr Val Pro Leu Glu Trp Gly Lys Asn Leu Ser
1               5                   10                  15

Ala Ser Asn Pro Leu Gly Phe Leu Pro Asp His Gln Leu Asp Pro Ala
                20                  25                  30

Phe Arg Ala Asn Thr Asn Asn Pro Asp Trp Asp Phe Asn Pro Lys Lys
                35                  40                  45

Asp Pro Trp Pro Glu Ala Asn Lys Val Gly Val Gly Ala Tyr Gly Pro
        50                  55                  60

Gly Phe Thr Pro Pro His Gly Gly Leu Leu Gly Trp Ser Pro Gln Ser
65                  70                  75                  80

Gln Gly Thr Leu Thr Thr Leu Pro Ala Asp Pro Pro Ala Ser Thr
                85                  90                  95

Asn Arg Gln Ser Gly Arg Gln Pro Thr Pro Ile Ser Pro Pro Leu Arg
                100                 105                 110

Asp Ser His Pro Gln Ala
```

115

<210> SEQ ID NO 10
<211> LENGTH: 108
<212> TYPE: PRT
<213> ORGANISM: Hepatitis B virus

<400> SEQUENCE: 10

Met Gly Gln Asn His Ser Val Thr Asn Pro Leu Gly Phe Phe Pro Asp
1               5                   10                  15

His Gln Leu Asp Pro Leu Phe Arg Ala Asn Ser Asn Asn Pro Asp Trp
            20                  25                  30

Asp Phe Asn Pro Asn Lys Asp Thr Trp Pro Glu Ala Thr Lys Val Gly
        35                  40                  45

Val Gly Ala Phe Gly Pro Gly Phe Thr Pro Pro His Gly Gly Leu Leu
    50                  55                  60

Gly Trp Ser Pro Gln Ala Gln Gly Ile Leu Thr Thr Leu Pro Ala Ala
65                  70                  75                  80

Pro Pro Pro Ala Ser Thr Asn Arg Gln Ser Gly Arg Lys Ala Thr Pro
                85                  90                  95

Ile Ser Pro Pro Leu Arg Asp Thr His Pro Gln Ala
            100                 105

<210> SEQ ID NO 11
<211> LENGTH: 119
<212> TYPE: PRT
<213> ORGANISM: Hepatitis B virus

<400> SEQUENCE: 11

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala
        115

<210> SEQ ID NO 12
<211> LENGTH: 108
<212> TYPE: PRT
<213> ORGANISM: Hepatitis B virus

<400> SEQUENCE: 12

Met Gly Gln Asn Leu Ser Val Ser Asn Pro Leu Gly Phe Phe Pro Glu
1               5                   10                  15

His Gln Leu Asp Pro Leu Phe Arg Ala Asn Thr Asn Asn Pro Asp Trp
            20                  25                  30

Asp Phe Asn Pro Asn Lys Asp Thr Trp Pro Glu Ala Thr Lys Val Gly
        35                  40                  45

```
Val Gly Ala Phe Gly Pro Gly Phe Thr Pro Pro His Gly Gly Leu Leu
 50                  55                  60

Gly Trp Ser Pro Gln Ala Gln Gly Val Thr Thr Ile Leu Pro Ala Val
 65                  70                  75                  80

Pro Pro Pro Ala Ser Thr Asn Arg Gln Ser Gly Arg Gln Pro Thr Pro
                 85                  90                  95

Ile Ser Pro Pro Leu Arg Asp Thr His Pro Gln Ala
            100                 105

<210> SEQ ID NO 13
<211> LENGTH: 108
<212> TYPE: PRT
<213> ORGANISM: Hepatitis B virus

<400> SEQUENCE: 13

Met Gly Leu Asn Gln Ser Thr Phe Asn Pro Leu Gly Phe Phe Pro Ser
 1               5                  10                  15

His Gln Leu Asp Pro Leu Phe Lys Ala Asn Ala Gly Ser Ala Asp Trp
             20                  25                  30

Asp Lys Asn Pro Asn Lys Asp Pro Trp Pro Gln Ala His Asp Thr Ala
         35                  40                  45

Val Gly Ala Phe Gly Pro Gly Leu Val Pro Pro His Gly Gly Leu Leu
 50                  55                  60

Gly Trp Ser Ser Gln Ala Gln Gly Leu Ser Val Thr Val Pro Asp Thr
 65                  70                  75                  80

Pro Pro Pro Pro Ser Thr Asn Arg Asp Lys Gly Arg Lys Pro Thr Pro
                 85                  90                  95

Ala Thr Pro Pro Leu Arg Asp Thr His Pro Gln Ala
            100                 105

<210> SEQ ID NO 14
<211> LENGTH: 21
<212> TYPE: PRT
<213> ORGANISM: Hepatitis B virus

<400> SEQUENCE: 14

Lys Lys Lys Asn Leu Ser Thr Ser Asn Pro Leu Gly Phe Phe Pro Asp
 1               5                  10                  15

His Gln Leu Pro Asp
             20

<210> SEQ ID NO 15
<211> LENGTH: 21
<212> TYPE: PRT
<213> ORGANISM: Hepatitis B virus

<400> SEQUENCE: 15

Lys Lys Lys Asn Leu Ser Thr Ser Asn Pro Leu Gly Phe Phe Pro Asp
 1               5                  10                  15

His Gln Leu Asp Pro
             20

<210> SEQ ID NO 16
<211> LENGTH: 5
<212> TYPE: PRT
<213> ORGANISM: Hepatitis B virus
<220> FEATURE:
<221> NAME/KEY: VARIANT
<222> LOCATION: (2)..(2)
<223> OTHER INFORMATION: Arbitrary amino acid, preferably L , I or Q,
```

```
      more preferably L
<220> FEATURE:
<221> NAME/KEY: VARIANT
<222> LOCATION: (4)..(4)
<223> OTHER INFORMATION: Arbitrary amino acid, preferably T, V, A or is
      not present, more preferably T or V, even more preferably T
<220> FEATURE:
<221> NAME/KEY: VARIANT
<222> LOCATION: (5)..(5)
<223> OTHER INFORMATION: Arbitrary amino acid, preferably P, S, T or F,
      more preferably P or S, even more preferably S

<400> SEQUENCE: 16

Asn Xaa Ser Xaa Xaa
1               5

<210> SEQ ID NO 17
<211> LENGTH: 6
<212> TYPE: PRT
<213> ORGANISM: Hepatitis B virus
<220> FEATURE:
<221> NAME/KEY: VARIANT
<222> LOCATION: (1)..(1)
<223> OTHER INFORMATION: Arbitrary amino acid, preferably D, E or S,
      more preferably D or E, even more preferably D

<400> SEQUENCE: 17

Xaa His Gln Leu Asp Pro
1               5

<210> SEQ ID NO 18
<211> LENGTH: 18
<212> TYPE: PRT
<213> ORGANISM: Hepatitis B virus
<220> FEATURE:
<221> NAME/KEY: VARIANT
<222> LOCATION: (2)..(2)
<223> OTHER INFORMATION: Arbitrary amino acid, preferably L , I or Q,
      more preferably L
<220> FEATURE:
<221> NAME/KEY: VARIANT
<222> LOCATION: (4)..(4)
<223> OTHER INFORMATION: Arbitrary amino acid, preferably T, V, A or is
      not present, more preferably T or V, even more preferably T
<220> FEATURE:
<221> NAME/KEY: VARIANT
<222> LOCATION: (5)..(5)
<223> OTHER INFORMATION: Arbitrary amino acid, preferably P, S, T or F,
      more preferably P or S, even more preferably S
<220> FEATURE:
<221> NAME/KEY: VARIANT
<222> LOCATION: (11)..(11)
<223> OTHER INFORMATION: Arbitrary amino acid, preferably F or L, more
      preferably F
<220> FEATURE:
<221> NAME/KEY: VARIANT
<222> LOCATION: (11)..(11)
<223> OTHER INFORMATION: Arbitrary amino acid, preferably F or L, more
      preferably F
<220> FEATURE:
<221> NAME/KEY: VARIANT
<222> LOCATION: (13)..(13)
<223> OTHER INFORMATION: Arbitrary amino acid, preferably D, E or S,
      more preferably D or E, even more preferably D

<400> SEQUENCE: 18

Asn Xaa Ser Xaa Xaa Asn Pro Leu Gly Phe Xaa Pro Xaa His Gln Leu
1               5                   10                  15

Asp Pro

<210> SEQ ID NO 19
<211> LENGTH: 5
```

```
<212> TYPE: PRT
<213> ORGANISM: Hepatitis B virus

<400> SEQUENCE: 19

Gly Cys His Ala Lys
1               5

<210> SEQ ID NO 20
<211> LENGTH: 8
<212> TYPE: PRT
<213> ORGANISM: Hepatitis B virus

<400> SEQUENCE: 20

Arg Pro Leu Ala Leu Trp Arg Ser
1               5

<210> SEQ ID NO 21
<211> LENGTH: 20
<212> TYPE: PRT
<213> ORGANISM: Hepatitis B virus

<400> SEQUENCE: 21

Lys Lys Lys Asn Leu Ser Ser Asn Pro Leu Gly Phe Phe Pro Asp His
1               5                  10                  15

Gln Leu Asp Pro
            20

<210> SEQ ID NO 22
<211> LENGTH: 12
<212> TYPE: PRT
<213> ORGANISM: Hepatitis B virus
<220> FEATURE:
<221> NAME/KEY: VARIANT
<222> LOCATION: (2)..(2)
<223> OTHER INFORMATION: Arbitrary amino acid, preferably L , I or Q,
      more preferably L
<220> FEATURE:
<221> NAME/KEY: VARIANT
<222> LOCATION: (4)..(4)
<223> OTHER INFORMATION: Arbitrary amino acid, preferably T, V, A or is
      not present, more preferably T or V, even more preferably T
<220> FEATURE:
<221> NAME/KEY: VARIANT
<222> LOCATION: (5)..(5)
<223> OTHER INFORMATION: Arbitrary amino acid, preferably P, S, T or F,
      more preferably P or S, even more preferably S
<220> FEATURE:
<221> NAME/KEY: VARIANT
<222> LOCATION: (11)..(11)
<223> OTHER INFORMATION: Arbitrary amino acid, preferably F or L, more
      preferably F

<400> SEQUENCE: 22

Asn Xaa Ser Xaa Xaa Asn Pro Leu Gly Phe Xaa Pro
1               5                  10

<210> SEQ ID NO 23
<211> LENGTH: 13
<212> TYPE: PRT
<213> ORGANISM: Hepatitis B virus
<220> FEATURE:
<221> NAME/KEY: VARIANT
<222> LOCATION: (6)..(6)
<223> OTHER INFORMATION: Arbitrary amino acid, preferably F or L, more
      preferably F
<220> FEATURE:
<221> NAME/KEY: VARIANT
<222> LOCATION: (8)..(8)
<223> OTHER INFORMATION: Arbitrary amino acid, preferably D, E or S,
      more preferably D or E, even more preferably D
```

```
<400> SEQUENCE: 23

Asn Pro Leu Gly Phe Xaa Pro Xaa His Gln Leu Asp Pro
1               5                   10
```